(12) United States Patent
Carbunaru et al.

(10) Patent No.: US 8,994,325 B2
(45) Date of Patent: Mar. 31, 2015

(54) EXTERNAL CHARGER FOR AN IMPLANTABLE MEDICAL DEVICE HAVING AT LEAST ONE MOVEABLE CHARGING COIL

(75) Inventors: Rafael Carbunaru, Valley Village, CA (US); Andrew DiGiore, San Francisco, CA (US); Todd Whitehurst, Frederick, MD (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 414 days.

(21) Appl. No.: 13/277,522

(22) Filed: Oct. 20, 2011

(65) Prior Publication Data

US 2012/0119699 A1     May 17, 2012

Related U.S. Application Data

(60) Provisional application No. 61/414,616, filed on Nov. 17, 2010.

(51) Int. Cl.
| | |
|---|---|
| H01M 10/44 | (2006.01) |
| H01M 10/46 | (2006.01) |
| H02J 7/02 | (2006.01) |
| H02J 7/00 | (2006.01) |
| H01F 38/14 | (2006.01) |

(52) U.S. Cl.
CPC .............. *H02J 7/025* (2013.01); *H02J 7/0042* (2013.01); *H01F 38/14* (2013.01)
USPC ......................................................... 320/108

(58) Field of Classification Search
USPC ......................................... 320/108, 107, 114
See application file for complete search history.

(56) References Cited

U.S. PATENT DOCUMENTS

| | | | | |
|---|---|---|---|---|
| 7,286,880 | B2 * | 10/2007 | Olson et al. | 607/61 |
| 7,948,208 | B2 * | 5/2011 | Partovi et al. | 320/108 |
| 7,952,322 | B2 * | 5/2011 | Partovi et al. | 320/108 |
| 8,169,185 | B2 * | 5/2012 | Partovi et al. | 320/108 |
| 8,242,741 | B2 * | 8/2012 | Phelps, III | 320/108 |
| 8,248,028 | B2 * | 8/2012 | Toya et al. | 320/108 |
| 8,362,744 | B2 * | 1/2013 | Terao et al. | 320/108 |
| 8,410,751 | B2 * | 4/2013 | Terao et al. | 320/108 |
| 8,432,129 | B2 * | 4/2013 | Lee et al. | 320/108 |

(Continued)

FOREIGN PATENT DOCUMENTS

WO    2006/010013    1/2006

OTHER PUBLICATIONS

U.S. Appl. No. 13/099,906, filed May 3, 2011, Carbunaru, et al.

*Primary Examiner* — Edward Tso
(74) *Attorney, Agent, or Firm* — Lewis & Reese, PLLC

(57) ABSTRACT

Improved external chargers for charging an implantable medical device, and particularly useful in charging a plurality of such devices, are disclosed. Each of the various embodiments include design elements for mechanically manipulating the position of one or more charging coils within the external charger to customize the magnetic charging field as appropriate for the charger/implantable device environment. For example, a single charging coil may be moved within a housing of the external charger to direct the charging field of the coil towards the currently "coldest" implant, i.e., the implant with the lowest coupling to the external charger. The one or more charging coils may be mechanically manipulated within the external charger housing in a number of ways, including by using linear actuators, by inflatable bladders, or even by hand.

35 Claims, 27 Drawing Sheets

(56) References Cited

U.S. PATENT DOCUMENTS

| | | |
|---|---|---|
| 2008/0027293 A1 | 1/2008 | Vodermayer et al. |
| 2008/0172109 A1 | 7/2008 | Rahman et al. |
| 2009/0069869 A1 | 3/2009 | Stouffer et al. |
| 2009/0096413 A1* | 4/2009 | Partovi et al. ............ 320/108 |
| 2009/0112291 A1 | 4/2009 | Wahlstrand et al. |
| 2010/0204756 A1 | 8/2010 | Aghassian |
| 2010/0244584 A1* | 9/2010 | Azancot et al. ............ 307/104 |
| 2010/0268309 A1 | 10/2010 | Parramon et al. |
| 2010/0270970 A1* | 10/2010 | Toya et al. ............ 320/108 |
| 2011/0004278 A1 | 1/2011 | Aghassian et al. |
| 2011/0093048 A1 | 4/2011 | Aghassian |
| 2011/0121777 A1 | 5/2011 | Carbumaru et al. |

* cited by examiner

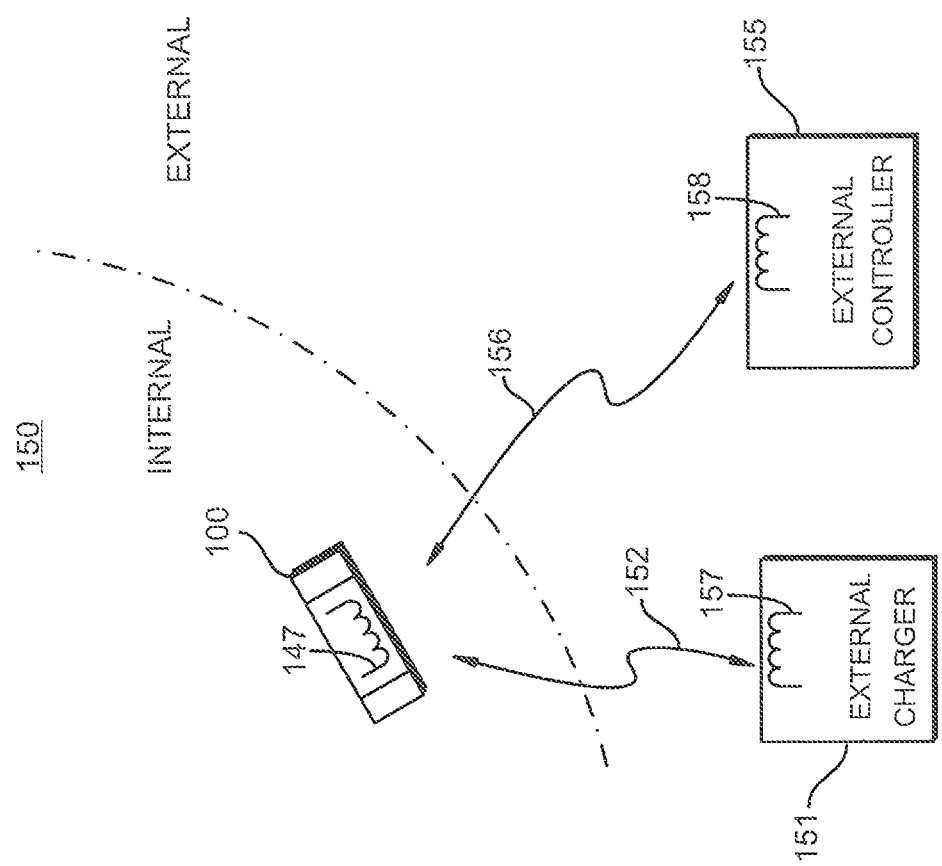

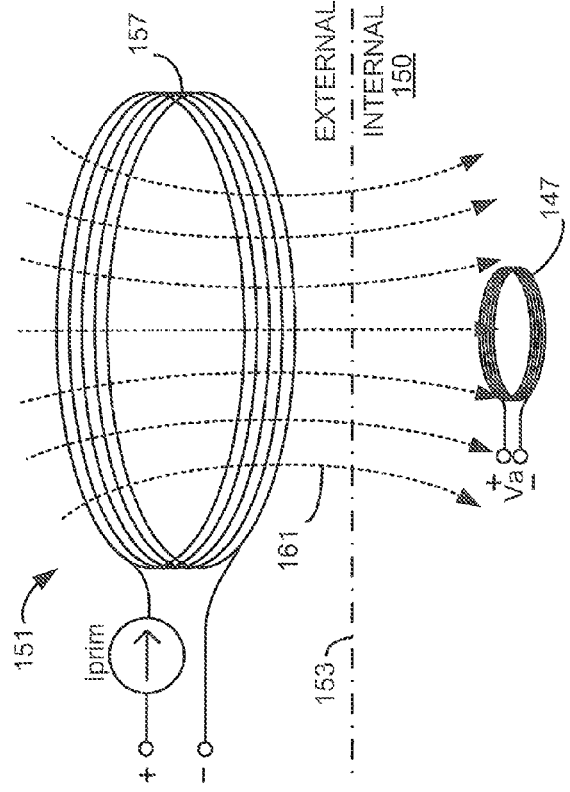
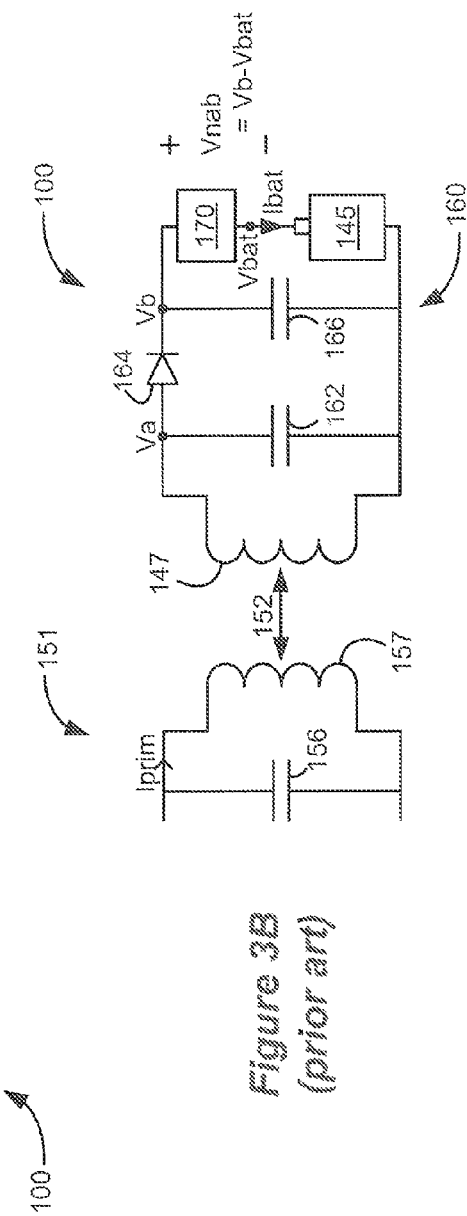
Figure 3A (prior art)
Figure 3B (prior art)

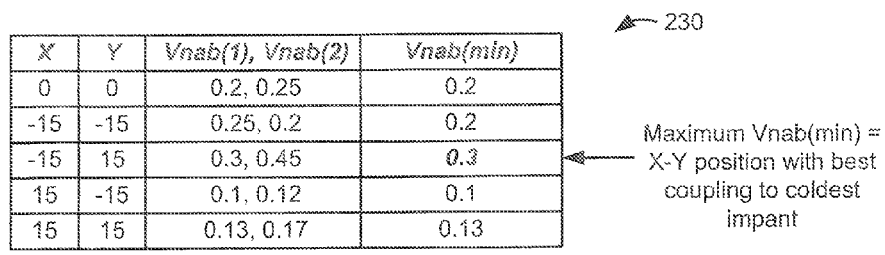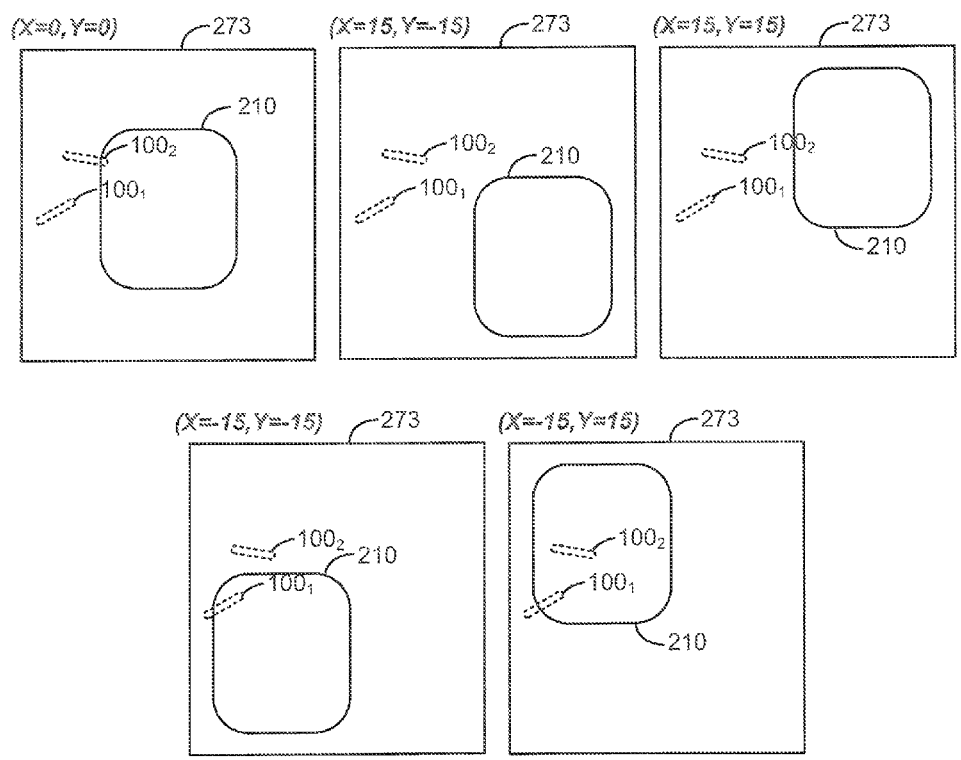
*Figure 5E*

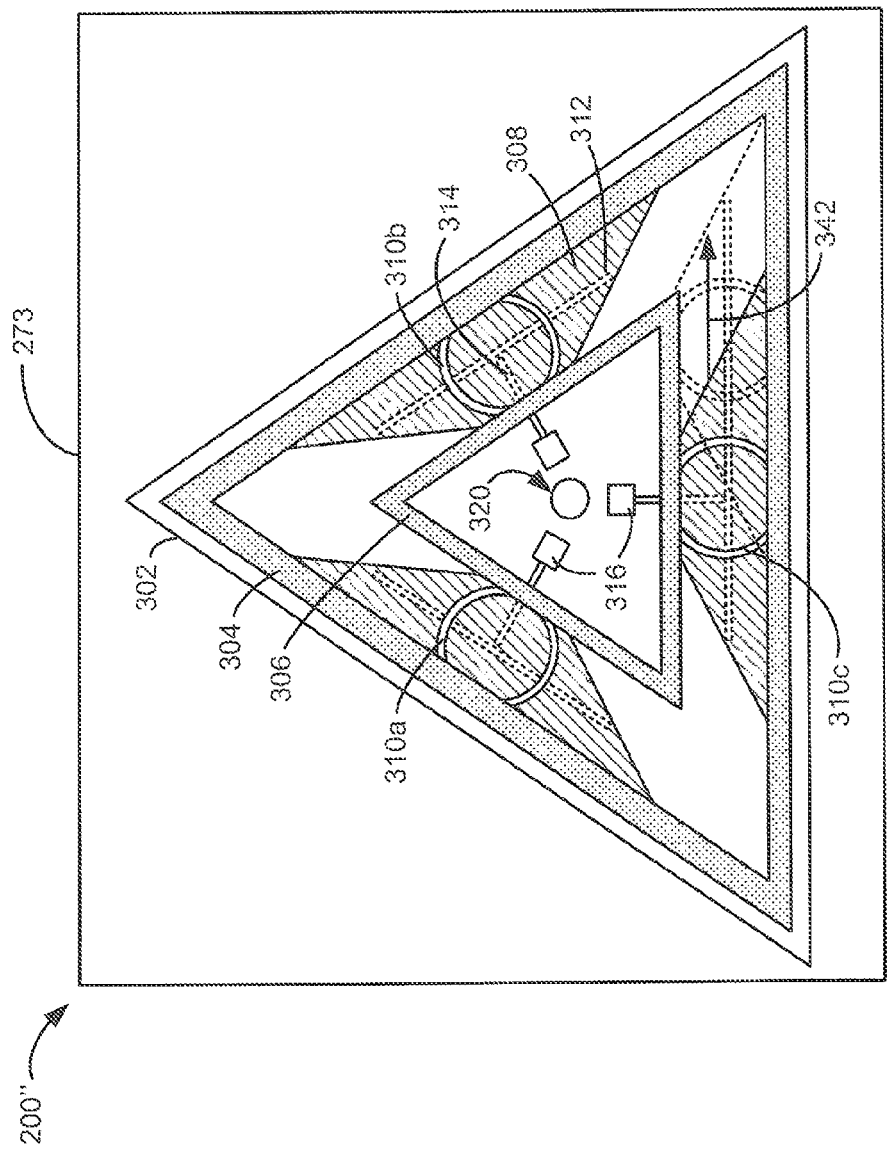

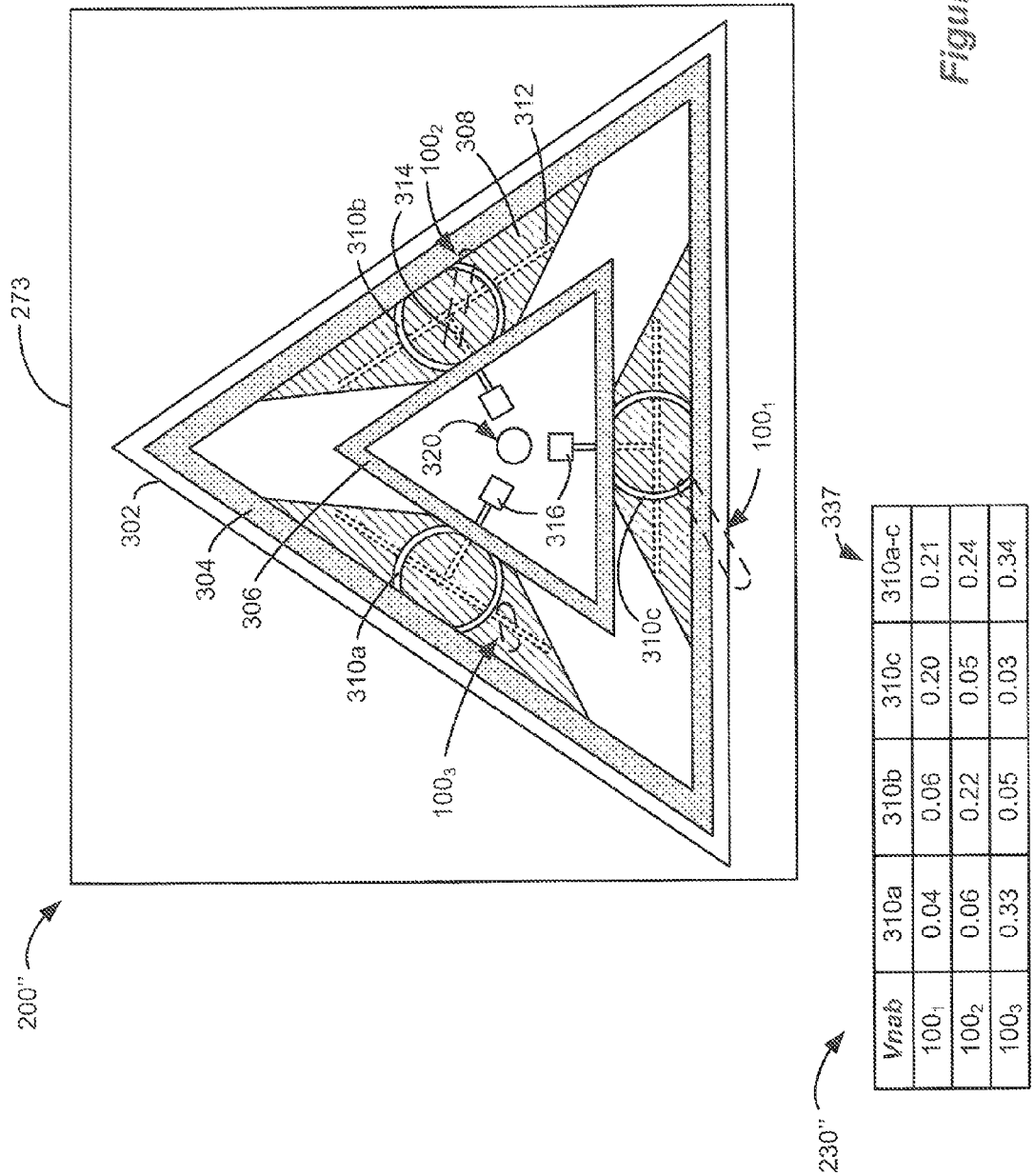

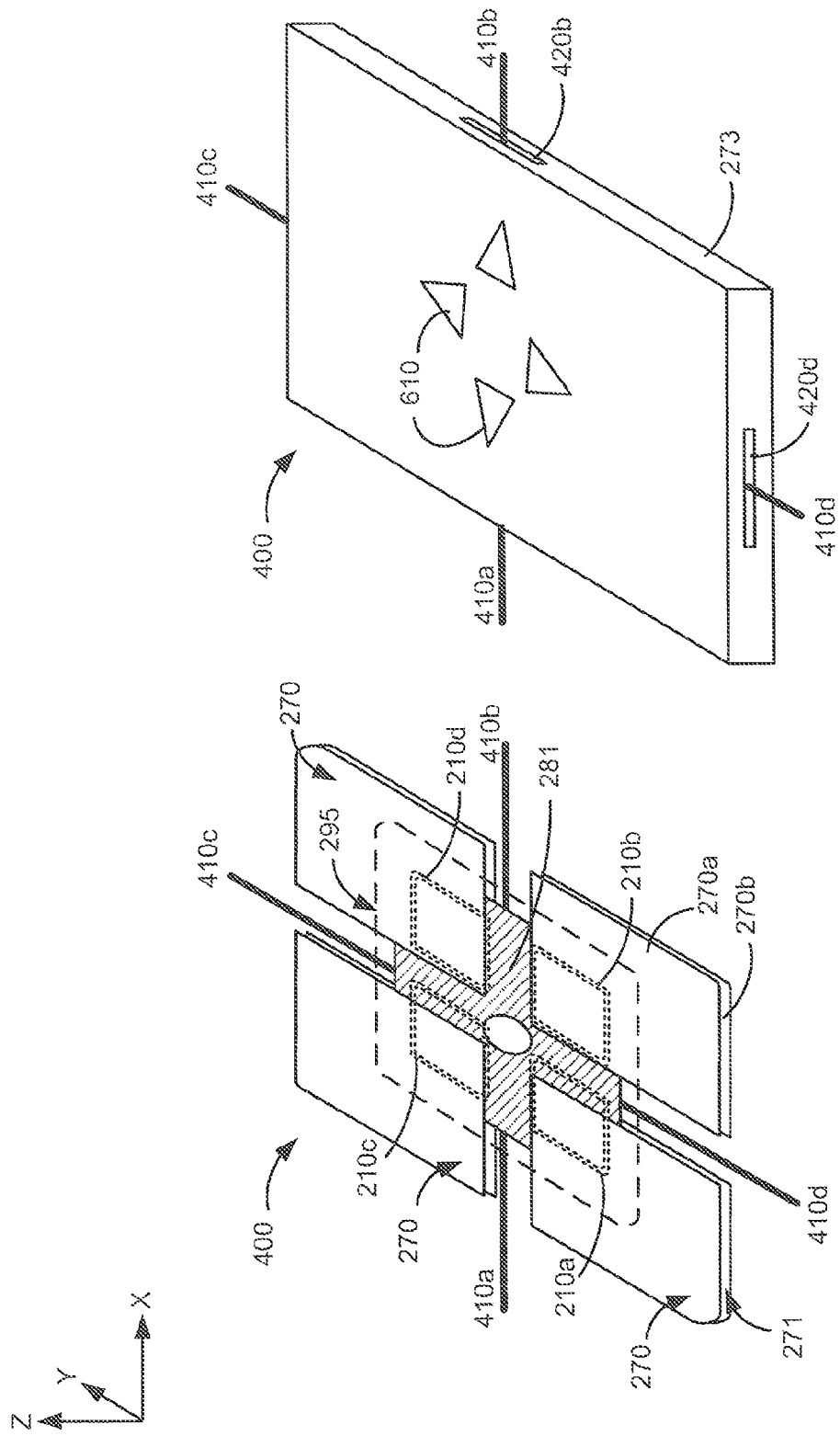

EXTERNAL CHARGER FOR AN IMPLANTABLE MEDICAL DEVICE HAVING AT LEAST ONE MOVEABLE CHARGING COIL

CROSS REFERENCE TO RELATED APPLICATIONS

This is a non-provisional application of U.S. Provisional Patent Application Ser. No. 61/414,616, filed Nov. 17, 2010, to which priority is claimed, and which is incorporated herein by reference.

FIELD OF THE INVENTION

The present invention relates generally to external chargers used to inductively charge one or more implantable medical devices such as neurostimulators.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder subluxation, etc. The present invention may find applicability in all such applications and in other implantable medical device systems, although the description that follows will generally focus on the use of the invention in a Bion® microstimulator device system of the type disclosed in U.S. Patent Application Publication 2010/0268309.

Microstimulator devices typically comprise a small, generally-cylindrical housing which carries electrodes for producing a desired stimulation current. Devices of this type are implanted proximate to the target tissue to allow the stimulation current to stimulate the target tissue to provide therapy for a wide variety of conditions and disorders. A microstimulator usually includes or carries stimulating electrodes intended to contact the patient's tissue, but may also have electrodes coupled to the body of the device via a lead or leads. A microstimulator may have two or more electrodes. Microstimulators benefit from simplicity. Because of their small size, the microstimulator can be directly implanted at a site requiring patient therapy.

FIG. 1 illustrates an exemplary implantable microstimulator 100. As shown, the microstimulator 100 includes a power source 145 such as a battery, a programmable memory 146, electrical circuitry 144, and a coil 147. These components are housed within a capsule 202, which is usually a thin, elongated cylinder, but may also be any other shape as determined by the structure of the desired target tissue, the method of implantation, the size and location of the power source 145, and/or the number and arrangement of external electrodes 142. In some embodiments, the volume of the capsule 202 is substantially equal to or less than three cubic centimeters.

The battery 145 supplies power to the various components within the microstimulator 100, such as the electrical circuitry 144 and the coil 147. The battery 145 also provides power for therapeutic stimulation current sourced or sunk from the electrodes 142. The power source 145 may be a primary battery, a rechargeable battery, a capacitor, or any other suitable power source. Systems and methods for charging a rechargeable battery 145 will be described further below.

The coil 147 is configured to receive and/or emit a magnetic field that is used to communicate with, or receive power from, one or more external devices that support the implanted microstimulator 100, examples of which will be described below. Such communication and/or power transfer may be transcutaneous as is well known.

The programmable memory 146 is used at least in part for storing one or more sets of data, including electrical stimulation parameters that are safe and efficacious for a particular medical condition and/or for a particular patient. Electrical stimulation parameters control various parameters of the stimulation current applied to a target tissue including the frequency, pulse width, amplitude, burst pattern (e.g., burst on time and burst off time), duty cycle or burst repeat interval, ramp on time and ramp off time of the stimulation current, etc.

The illustrated microstimulator 100 includes electrodes 142-1 and 142-2 on the exterior of the capsule 202. The electrodes 142 may be disposed at either end of the capsule 202 as illustrated, or placed along the length of the capsule. There may also be more than two electrodes arranged in an array along the length of the capsule. One of the electrodes 142 may be designated as a stimulating electrode, with the other acting as an indifferent electrode (reference node) used to complete a stimulation circuit, producing monopolar stimulation. Or, one electrode may act as a cathode while the other acts as an anode, producing bipolar stimulation. Electrodes 142 may alternatively be located at the ends of short, flexible leads. The use of such leads permits, among other things, electrical stimulation to be directed to targeted tissue(s) a short distance from the surgical fixation of the bulk of the device 100.

The electrical circuitry 144 produces the electrical stimulation pulses that are delivered to the target nerve via the electrodes 142. The electrical circuitry 144 may include one or more microprocessors or microcontrollers configured to decode stimulation parameters from memory 146 and generate the corresponding stimulation pulses. The electrical circuitry 144 will generally also include other circuitry such as the current source circuitry, the transmission and receiver circuitry coupled to coil 147, electrode output capacitors, etc.

The external surfaces of the microstimulator 100 are preferably composed of biocompatible materials. For example, the capsule 202 may be made of glass, ceramic, metal, or any other material that provides a hermetic package that excludes water but permits passage of the magnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The microstimulator 100 may also include one or more infusion outlets 201, which facilitate the infusion of one or more drugs into the target tissue. Alternatively, catheters may be coupled to the infusion outlets 201 to deliver the drug therapy to target tissue some distance from the body of the microstimulator 100. If the microstimulator 100 is configured to provide a drug stimulation using infusion outlets 201, the microstimulator 100 may also include a pump 149 that is configured to store and dispense the one or more drugs.

Turning to FIG. 2, the microstimulator 100 is illustrated as implanted in a patient 150, and further shown are various external components that may be used to support the implanted microstimulator 100. An external controller 155 may be used to program and test the microstimulator 100 via communication link 156. Such link 156 is generally a two-way link, such that the microstimulator 100 can report its status or various other parameters to the external controller 155. Communication on link 156 may occur, e.g., via magnetic inductive coupling. Thus, when data is to be sent from the external controller 155 to the microstimulator 100, a coil 158 in the external controller 155 is excited to produce a magnetic field that comprises the link 156, which magnetic field is detected at the coil 147 in the microstimulator. Likewise, when data is to be sent from the microstimulator 100 to the external controller 155, the coil 147 is excited to produce a magnetic field that comprises the link 156, which magnetic field is detected at the coil 158 in the external controller. Typically, the magnetic field is modulated, for example with Frequency Shift Keying (FSK) modulation or the like, to encode the data. The external controller 155 is typically sized to be a hand-holdable device containing a user interface for controlling and monitoring its operation, as is well known in the art.

An external charger 151 provides power used to recharge the battery 145 (FIG. 1). Such power transfer occurs by energizing the coil 157 in the external charger 151, which produces a magnetic field comprising link 152. This magnetic field 152 energizes the coil 147 through the patient 150's tissue, and which is rectified, filtered, and used to recharge the battery 145 as explained further below. Link 152, like link 156, can be bidirectional to allow the microstimulator 100 to report status information back to the external charger 151. For example, once the circuitry 144 in the microstimulator 100 detects that the power source 145 is fully charged, the coil 147 can signal that fact back to the external charger 151 so that charging can cease. Charging can occur at convenient intervals for the patient 150, such as every night. Like the external controller 155, the external charger 151 is typically a hand held device containing a user interface for controlling and monitoring its operation, again as is well known in the art.

FIGS. 3A and 3B illustrate salient portions of the microstimulator's power circuitry 160. When the coil 157 in the external charger 151 is stimulated by AC current Iprim, a magnetic charging field 161 is produced. This field 161 (comprising part of link 152) is received at coil 147 in the microstimulator 100. The coil 147 in combination with capacitor 162 comprises a resonant circuit, or tank circuit, which produces an AC voltage at Va. This AC voltage is rectified by rectifier circuitry 164, which can comprise a well-known four-diode bridge circuit, although it is shown in FIG. 3B as a single diode for simplicity. Capacitor 166 assists to filter the signal at node Vb, such that Vb is essentially a DC voltage, although perhaps having a negligible ripple. Intervening between Vb and the rechargeable battery 145 is charging circuitry 170, which ultimately takes the DC voltage Vb and uses it to produce a controlled battery charging current, Ibat. Charging circuitry 170 is well known. One skilled in the art will recognize that the power circuitry 160 may include other components not shown for simplicity.

Also shown in FIG. 3B is a parameter called Vnab. Vnab comprises a voltage in the power circuitry 160 within the implant 100, and in particular comprises a voltage drop across the charging circuitry 170 when the power circuitry 160 is receiving a magnetic charging field. Vnab is computed as the difference between the DC rectified voltage, Vb, and the battery voltage, Vbat, i.e., Vnab=Vb−Vbat. As explained in U.S. Patent Application Publication 2011/0121777 ("the '777 Publication"), which is incorporated herein by reference in its entirety, Vnab scales with the power received from the external charger. Because the degree of coupling will affect the receipt of such power, Vnab is indicative of the coupling. As such, Vnab can comprise (or can be used to derive) a coupling parameter between the external charger 151 and the microstimulator 100. Note that Vnab takes into account all factors affecting coupling, including distance, offset, and angle between the coils in the microstimulator and the external charger.

Depending on the patient's condition, it may be desirable to implant more than one microstimulator to provide more complex stimulation to the patient and/or to provide stimulation in different locations. For instance, as shown in FIG. 4, a first microstimulator $100_1$ is implanted at a first location, and a second microstimulator $100_2$ is implanted at a second location. Additional microstimulators could also be implanted if more complicated therapies are indicated, but only two microstimulators are shown in FIG. 4 for simplicity. Microstimulators $100_1$ and $100_2$ may operate independently or may operate in a coordinated manner.

The external controller 155 can communicate with each microstimulator independently, with communications accompanied by a header containing an address of the microstimulator. Such addressing ensures no confusion when communicating with the two microstimulators $100_1$ and $100_2$, and thus allows each to be independently programmed and monitored by the external controller 155. Such addressing also allows the two microstimulators $100_1$ and $100_2$ to communicate with each other.

Both microstimulators $100_1$ and $100_2$ will eventually need to have their batteries recharged using external charger 151, and such charging presents special challenges. Each of the microstimulators $100_1$ and $100_2$ could be charged independently, but this would take additional time. Even if a patient had only two microstimulators implanted, the total time to charge both would roughly double compared to a single implant, which would comprise a major inconvenience to the patient. Independent charging of the microstimulators also requires some coordination between the microstimulators $100_1$ and $100_2$. For example, the microstimulators $100_1$ and $100_2$ would have to know when to enable or disable charging by opening or connecting their coils 147.

Because of such issues, the inventors consider it preferable to charge both microstimulators $100_1$ and $100_2$ at the same time. However, while this approach would provide for faster charging, it is a challenge to optimize and to do so safely. Of particular concern is implant heating, which one skilled in the art will understand is an inevitable side effect of charging using magnetic fields. Heating can result from several different sources, such as eddy currents in conductive portions of the implant, or heating of the various components in the power circuitry 160. Implant heating is a serious safety concern; if an implant exceeds a given safe temperature (e.g., 41° C.), the tissue surrounding the implant may be aggravated or damaged.

Generally speaking, implant heating is a function of both the strength of the magnetic charging field, and the coupling between the external charger 151 and the implant. The strength of the magnetic charging field can be increased by increasing the excitation current, Iprim, in the coil 157 of the external charger 151 (FIGS. 3A and 3B). Increasing the magnetic charging field will increase the current/voltage induced in the coil 147 of the microstimulator 100, which increases the battery charging current, Ibat (FIG. 3B). Increasing the battery charging current speeds up charging, but also increases heat dissipation in the device.

Coupling between the external charger 151 and the implant affects how readily the magnetic charging field is passed to the implant, i.e., how strongly the effect of the magnetic charging field is felt at the implant. Many factors affecting coupling, such as the inductances of the coil 157 in the external charger 151 and the coil 147 in the implant; alignment, angle and distance between the coils 151 and 147; the permittivity of any materials (e.g., tissue, air) between the coils, etc. Generally speaking, if the coupling between the coils is relatively high, a relatively large current/voltage will be induced in implant coil 147, leading to faster charging and higher power dissipation (higher temperatures) in the implant.

Because of differences in the placement of multiple microstimulators in a patient, one could expect that the coupling between the external charger 151 and each of those microstimulators would differ. This means that the same magnetic charging field produced by the external charger 151 would result in different amounts of power dissipation in each of the microstimulators. Consider FIG. 4: microstimulator $100_2$ is located deeper in the patient, and is therefore farther away from the external charger 151 than is microstimulator $100_1$. Moreover, the angle θ between the coil 147 in microstimulator $100_2$ and coil 157 in external charger 151 is relatively large, and the offset of their axes D is relatively large. These factors all contribute to low coupling between the external charger 157 and microstimulator $100_2$ as compared to microstimulator $100_1$.

As a result, when the external charger 151 produces a magnetic charging field, microstimulator $100_1$ will charge more quickly—and will generate more heat—than will microstimulator $100_2$. As noted, this makes optimization difficult. If the generated magnetic charging field is optimized to charge microstimulator $100_2$ as quickly as possible at a safe temperature, then microstimulator $100_1$ would become too hot. By contrast, if the generated magnetic charging field is optimized to charge microstimulator $100_1$ as quickly as possible at a safe temperature, then microstimulator $100_2$ would charge too slowly.

BRIEF DESCRIPTION OF THE DRAWINGS

FIG. 2 illustrates the implant in communication with, inter alia, an external charger, in accordance with the prior art.

FIGS. 3A and 3B illustrates the operation of charging circuitry within the implant and external charger, in accordance with the prior art.

FIGS. 5A-5E illustrate the structure and operation of a first embodiment of an improved external charger comprising a mechanically positionable charging coil.

FIGS. 7A-7G illustrate the structure and operation of a third embodiment of an improved external charger comprising a plurality of charging coils each independently mechanically positionable.

FIGS. 8A-8D illustrate the structure and operation of a fourth embodiment of an improved external charger comprising a plurality of charging coils mechanically positionable by hand.

DETAILED DESCRIPTION

Figure 1:
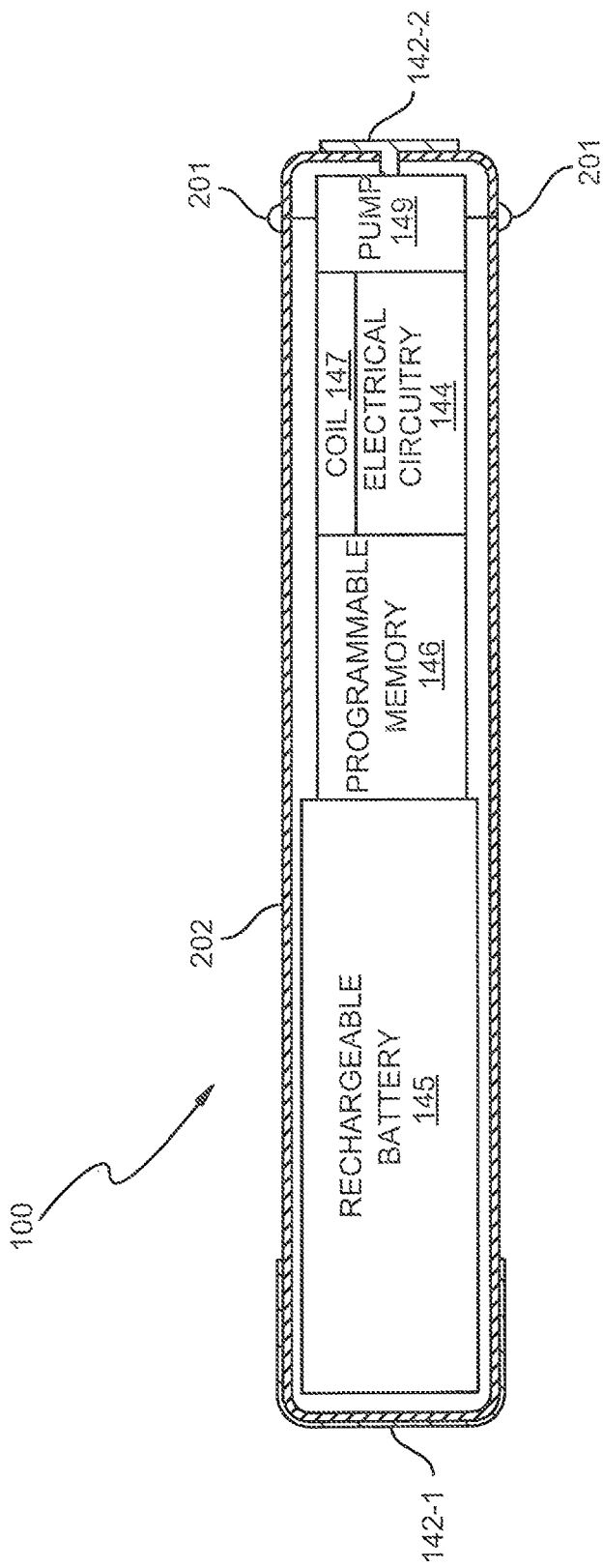
FIG. 1 illustrates a microstimulator implant, including a battery requiring recharging from an external charger, in accordance with the prior art.
Figure 4:
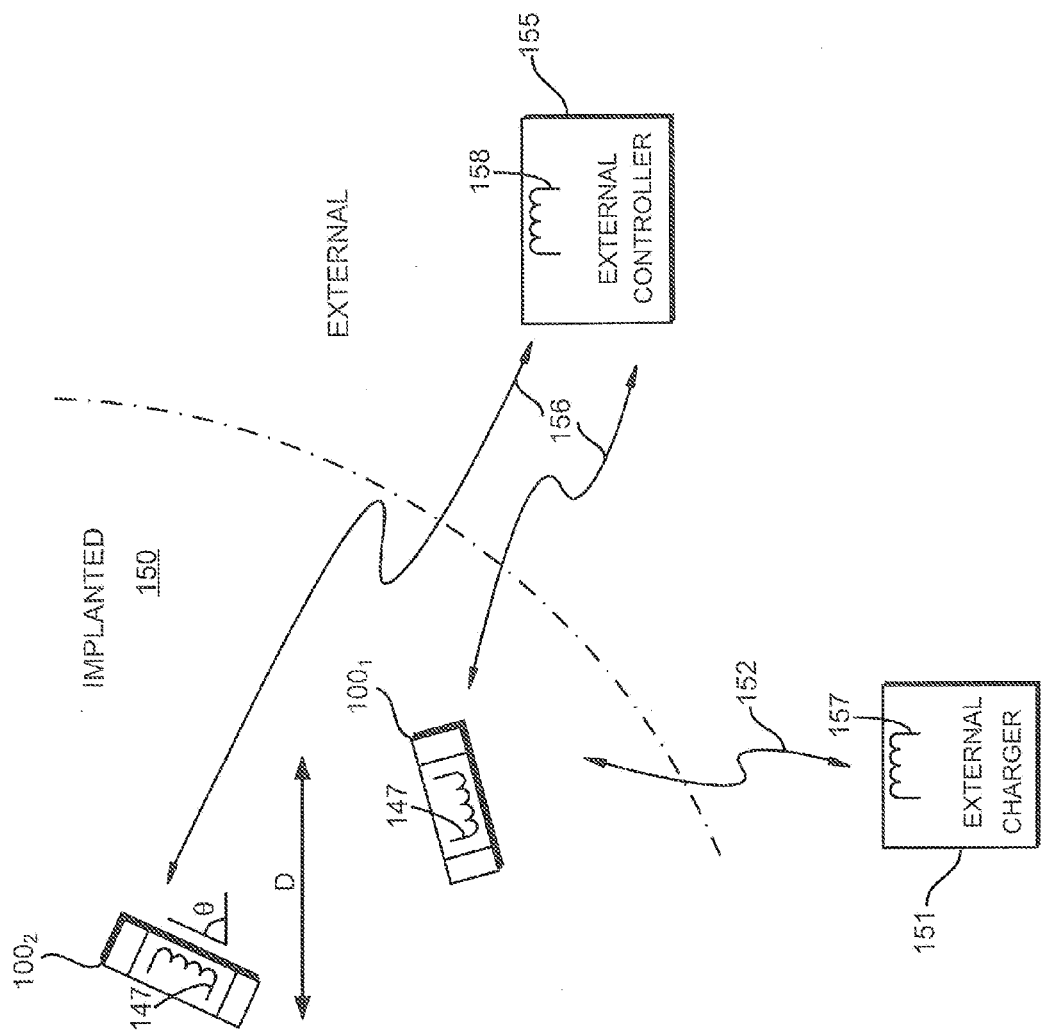
FIG. 4 illustrates multiple implants in communication with an external charger, in accordance with the prior art.

Improved external chargers for charging an implantable medical device, and particularly useful in charging a plurality of such devices, are disclosed. Each of the various embodiments include design elements for mechanically manipulating the position of one or more charging coils within the external charger to customize the magnetic charging field as appropriate for the charger/implantable device environment. For example, a single charging coil may be moved within a housing of the external charger to direct the charging field of the coil towards the currently "coldest" implant, i.e., the implant with the lowest coupling to the external charger, or away from the currently "hottest" implant, i.e., the implant with the highest coupling to the external charger. In another example, a plurality of charging coils may be moved within the external charger to direct the sum effect of their charging fields towards a cold implant and away from a hot implant. The one or more charging coils may be mechanically manipulated within the external charger housing in a number of ways, including by using linear actuators, by inflatable bladders, or even by hand. Mechanically customizing the magnetic field in the external charger allows multiple implants to be charged simultaneously and while mitigating concerns that implants having different couplings will charge at different speeds and temperatures. Mechanically customizing the magnetic field also benefits the charging of a single implant, which is especially useful if the implant and the charger are not well aligned.

FIGS. 5A to 5E illustrate a first embodiment of an improved external charger 200 particularly useful in charging a plurality of implantable medical devices. As shown in cross-section in FIG. 5A, external charger 200 comprises a single charging coil 210 that is mechanically positionable within the external charger housing 273. Charger 200 additionally contains a battery 271, a main printed circuit board (PCB) 278, a coil plate 281, and a coil chassis 270. The external charger housing 273 is typically formed of a hard plastic, which may be divided into top and bottom halves securable together. Clamps 276 may be utilized to hold the main PCB 278 in place within the housing 273. Other aspects (e.g., the user interface) of external charger 200 that are unimportant to understanding the mechanical manipulation of the charging coil 210 are not shown.

The main PCB 278 preferably contains the bulk of the electronic circuitry 274 for the external charger 200, which circuitry 274 is preferably placed on the PCB 278 to minimize the generation of eddy currents when the external charger 200 is generating a magnetic field. Electronic circuitry 274 can include a microcontroller 300 (FIG. 5C). Battery 271 is shown coupled to the same side of the PCB 278 as the electronic circuitry 274, which side is opposite of the charging coil 210.

Charging coil 210 is affixed to coil plate 281 using an epoxy or other suitable means, and then placed within the coil chassis 270. (The coil plate 281 may conveniently be made from PCB material, even though no electronics other than the coil are affixed thereto. In recognition, it is referred to as coil PCB 281). Coil chassis 270 may be constructed from hard plastic or any other suitable material and affixed within the housing 273. The coil PCB 281 which carries the coil 210 is designed to move within the coil chassis 270 when acted upon by various mechanical actuators 208. Actuators 208 may comprise a motor, such as a linear actuators or small linear servomotors, having rods 209 abutting each of the four sides of the coil PCB 281 as shown in FIG. 5B. (The external charger housing 273 and certain other internal components are removed in FIG. 5B for easier viewing of internal components). In other embodiments, a larger or smaller number of actuators 208 may be used to mechanically position the coil 210.

A hole 282 is provided in the center of the PCB 281 to allow the ends 275 of the coil 210 to pass to the main PCB 278 where they can be soldered and connected to circuitry (see FIG. 5C) present on the PCB 278. The ends 275 should have sufficient slack to allow the coil PCB 281/coil 210 to move inside of the external charge housing 273 without compromising the electrical/mechanical contact of the ends 275 to the main PCB 278. The actuators 208 also have leads 207 that couple to actuator driver circuitry on the main PCB 278, although these leads 207 need not pass through hole 282, as explained below.

Figure 5A:
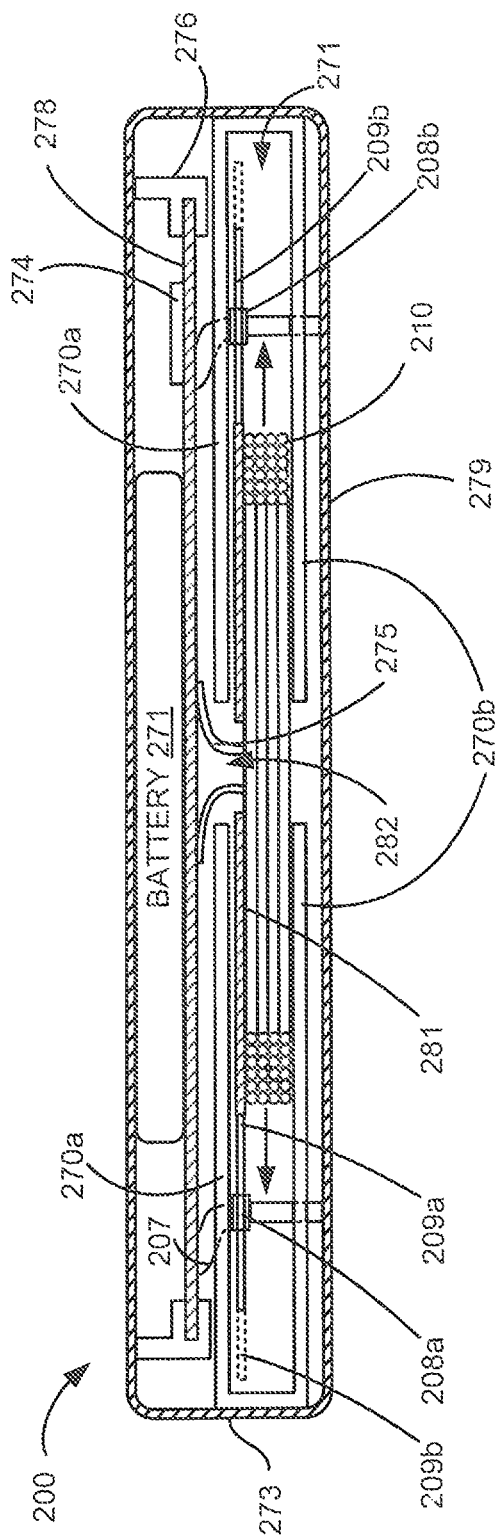
Figure 5B:
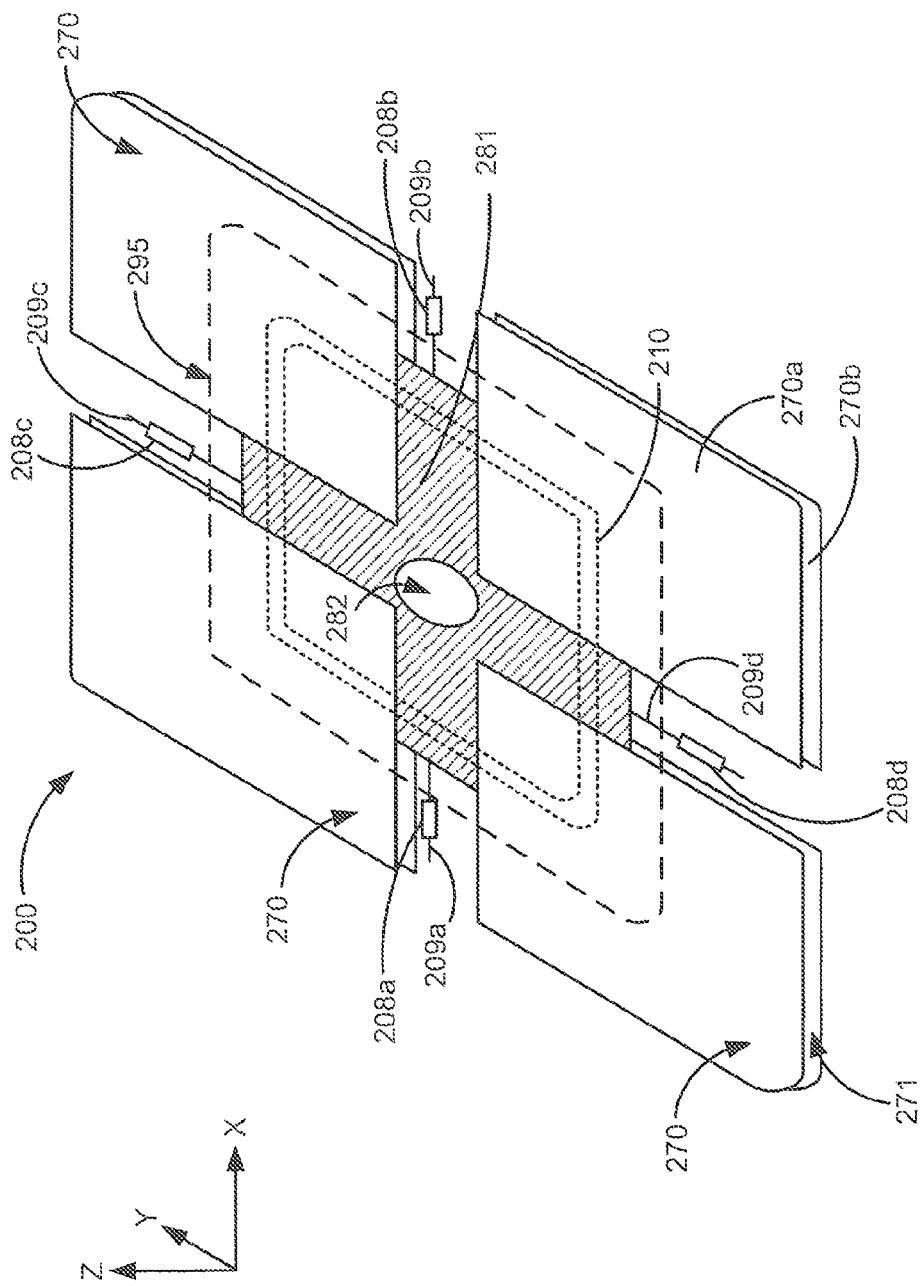
Figure 5C:
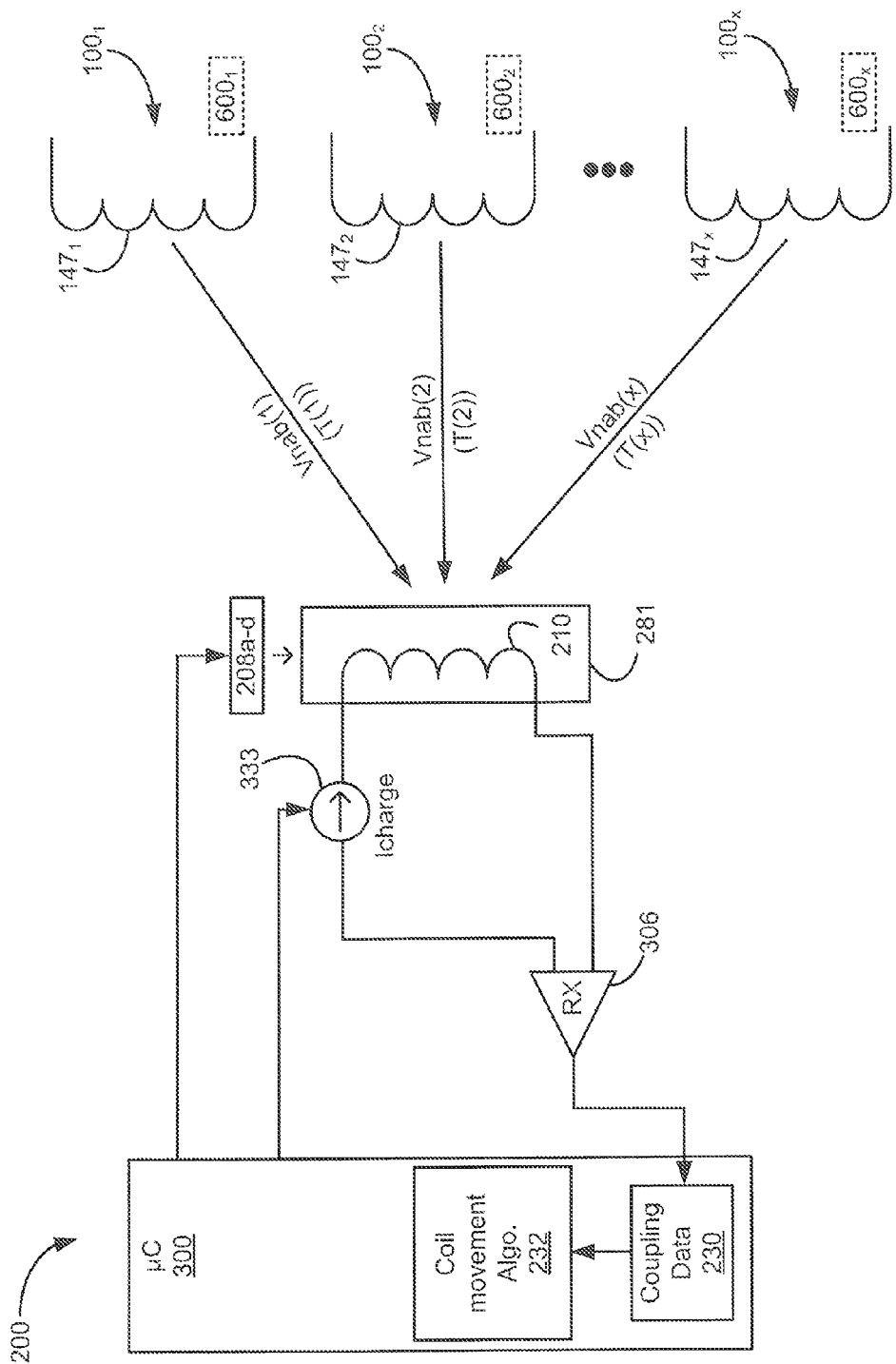

The coil chassis 270 as shown in FIGS. 5A and 5B can comprise upper 270*a* and lower 270*b* portions creating a track 271 large enough to accommodate the thickness of the coil PCB 281 and the coil 210. The coil PCB 281/coil 210 can move in X and Y directions within this track 271, thus allowing the coil 210 to be positioned roughly anywhere within a positioning area 295 as shown in FIG. 5B. Such X-Y movement is in the plane in which the coil 210 is wound, or in a plane parallel to a planar surface 279 of the housing 273 that is proximate to the patient while the external charger 200 is charging the patient's implant(s). The coil chassis 270 can be split into four corner portions, as best shown in FIG. 5B, which allows room for the actuators 208 and their leads 207. However, this is not strictly necessary, and the coil chassis 207 can be designed in other manners to facilitate X-Y movement of the charging coil 210.

FIG. 5A shows movement of the coil PCB 281/coil 210 within the coil chassis 270 via control of the actuators 208, and in particular two actuators 208*a* and 208*b* are shown to illustrate movement in the X direction. Each of actuators 208*a* and 208*b* can be affixed within the external charger 200 in different manners, such as to the bottom of the housing 273 as shown. Centered positions of actuator rods 209*a* and 209*b* are shown in solid lines, while the dashed lines represents potential positioning of the rods 209*a* and 209*b* upon activation of the actuators 208*a* and 208*b*. In some embodiments, the stroke length of the actuator rods 209*a* and 209*b* may be roughly 40 mm.

When two actuators 208 are used to move the coil PCB 281/coil 210 in a given direction, care should be taken to coordinate the actuation. For example, to move the coil 210 20 mm to the left, the rod 209*a* of actuator 208*a* may be retracted 20 mm, while the rod 209*b* of actuator 208*b* may simultaneously be extended by 20 mm. However, it is not required to have two actuators operating synchronously in this fashion. For example, there can be only one actuator/rod 208/209 (e.g., 208*a*/209*a*), with the other (208*b*/209*b*) replaced by a biasing means (e.g., a spring) between the edge of the coil PCB 281 and the edge of the coil chassis 270.

Note that while the actuator rods 209 engage the edges of the coil PCB 281, they are not rigidly affixed thereto, which allows for free movement of the PCB 281 in the X and Y directions. For example, should actuators 208*c* and 208*d* (FIG. 5B) be activated to move the coil PCB 281 in the Y direction, the PCB 281 would slide against the abutting edges of the rods 209*a* and 209*b* in the X direction.

FIG. 5C shows circuitry for positioning the coil PCB 281/ coil 210 in a proper position within the external charger housing 273, and further shows the coil 210 in relation to 'x' microstimulators 100 to be charged. A microcontroller 300 in the external charger 200 enables a current source 333 to issue an AC current (Icharge) through the coil 210. This current Icharge can comprise a test current issued during a testing phase, during which the coil 210 will be positioned within the external charge housing 273 prior to commencing an actual charging session. Or, Icharge can comprise the actual current used during the charging session, meaning that the coil 210 position will be adjusted "on the fly" during the charging session. One skilled in the art will understand that AC current Icharge can result from L-C resonance, although the capacitor involved is not shown for simplicity. The passage of Icharge through the coil 210 results in the generation of a magnetic field, which may comprise a test magnetic field or the actual charging magnetic field as just noted.

In response to receipt of the magnetic field from coil 210, each of the microstimulators 100 will determine a coupling parameter indicative of the strength of the received magnetic field from the coil 210, such as the Vnab coupling parameter from the above-referenced '777 Publication discussed in the Background of this disclosure. Each microstimulator 100 reports their Vnab coupling data back to the external charger 200 in the manner discussed in the above-referenced '777 Publication. For example, the microstimulators 100 can transmit the Vnab parameters using telemetry circuitry (not shown) otherwise used to communicate with an external controller 155 (FIG. 2), although in this case it will be the external charger 200 that receives and demodulated this transmission. Such telemetry circuits typically operate pursuant to a Frequency Shift Keying (FSK) communication protocol, as is well known. Or, the microstimulators 100 can use Load Shift Keying (LSK) in which the microstimulators 100 vary the resistances of their coils 147 to produce detectable reflections in the magnetic field. Still other telemetry protocols can be used to transmit the Vnab coupling data to the coil 157, and no particular telemetry protocol is important. Regardless of how the Vnab coupling parameters are transmitted to the coil 210, it is demodulated at receiver 306 and stored in the external charger 200 as coupling data 230. Such storage may comprise memory on-board the microcontroller 300, but this is not strictly necessary; any memory associated with the microcontroller 300 can be used to store the coupling data 230.

In another example, each of the microstimulators 100 can include temperatures sensors 600, as shown in dotted lines in FIG. 5C. Each of the temperature sensors 600 can measure the temperature of their respective microstimulators 100 during charging (or during testing). Because a better-coupled implant would become hotter in the presence of a magnetic field than would a poorly-coupled implant, the temperatures T(x) of each of the microstimulators 100 can be telemetered to the external charger 200 and used as the coupling data 230 instead of Vnab. The same is true in other subsequent examples, even though temperatures sensors 600 and temperature reporting are not included in those examples for simplicity.

Once the Vnab coupling data 230 is received, such data is analyzed by the microcontroller 300 to decide how logically to move the coil 210 to best charge the various microstimulators. Such decisions are made by a coil movement algorithm 232 operating within (or in conjunction with) the microcontroller 300. The manner in which coil movement algorithm 232 can work are varied and subject to designer preferences, but a logical goal of the algorithm 232 is to move the coil 210 to a position within the external charger housing 273 to best couple with a worst-coupled or "coldest" of the microstimulators 100, or to otherwise best unify the energy each of the microstimulators is receiving so that simultaneous charging occurs at a uniform rate between the various microstimulators.

Figure 5D:
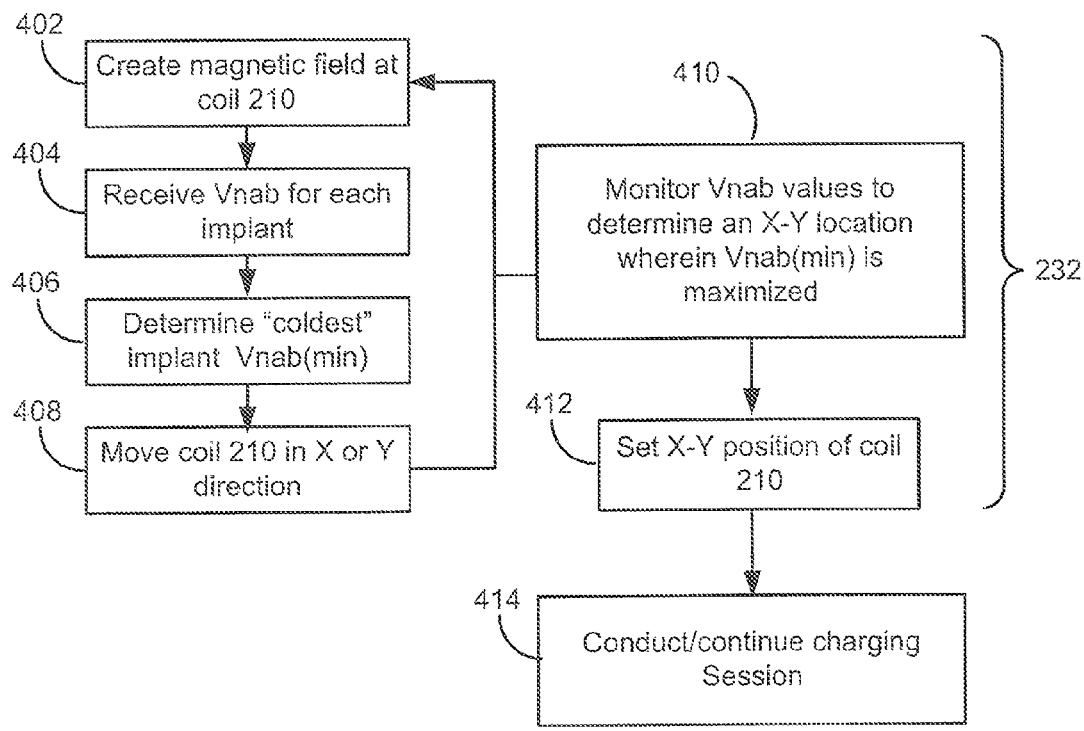

An example of coil movement algorithm 232 is illustrated in FIG. 5D in flow chart form. The goal of algorithm 232 is to move the coil 210 until the coupling to the "coldest" microstimulator is made as high as possible, i.e., to make Vnab(min) (the Vnab for the coldest microstimulator) as large as possible. In step 402, a magnetic field is created at coil 210 as just discussed, and the Vnab coupling values for each of the microstimulator 100 are received at the external charger 200 in step 404. In step 406, the coldest, worst-coupled microstimulator is determined, i.e., that with the smallest Vnab (Vnab(min)).

In step 408, the coil 210 is then moved in an X or Y direction, and the process repeated. Step 410 monitors the resulting Vnab values at different coil 210 locations to see whether Vnab(min) is maximizing. Once Vnab(mix) appears to be maximized, e.g., because continued coil movement fails to increase Vnab(min) significantly, the algorithm 232 infers that the current X-Y position of the coil 210 has the best coupling with the coldest implant, and that position is then set in step 412. Once set, the charging session can commence (if the proceeding steps were performed during a test phase), or continue (if coil positioning optimization was occurring during a charging session) in step 414.

How to move the coil 210 in step 408 can be accomplished in several different ways, but in one embodiment comprises an iterative process to intelligently search for an optimal X-Y position for the coil 210. One such process is shown in FIG. 5E for a simple case of two microstimulators $100_1$ and $100_2$. In this example, Vnab coupling measurements are taken at five evenly-spaced coil positions within the housing 273: a center position (X=0, Y=0), and four positions near to the corners of the housing 273 (X=+/−15 mm, Y=+/−15 mm). The relative positioning of the external charge housing 273, the coil 210, and the two implanted microstimulators $100_1$ and $100_2$ are shown in top-down views for each of the five coil positions. The reported coupling data 230 for each coil position is shown in the table. In this example, it is seen that the largest Vnab(min) occurs when the coil 210 is at location X=−15 mm, Y=15 mm, meaning that the coupling to the coldest implant (microstimulator $100_1$ in this case) is maximized, and suggesting that locating the coil 210 at or near this location would be optimal for the charging of both microstimulators $100_1$ and $100_2$. This is generally a sensible coil position, because the top down view at this location shows that the coil 210 is generally over both of the microstimulators 100. Once this general location is located, coil movement algorithm 232 can try further locations around this general location (e.g., (−13, 17), (−13, 13), (−17, 17), (−17, 13)) to try and "hone in" on an even further optimal location for charging the cold implant.

Step 408 of the coil movement algorithm 232 can also operate in other ways to search for an optimal coil position. For example, the coil 210 can be moved in small increments in +/−X and +/−Y increments starting from its center position to see in which direction Vnab(min) is increasing. The coil 210 can then be moved to that improved location, and the process repeated, so that the coil 210 is gradually "walked" to the optimal location.

While the external charger 200 has been illustrated as operable to charge a plurality of implants, note that it also provides benefit to charging a single implant. When only a single microstimulator 100 is being charged, it will always comprise the Vnab(min) at any given position of the coil 210. But by moving the coil 210 using coil movement algorithm 232, that Vnab value can still be maximized by moving the coil 210 into a better position relative to the single microstimulator 100, thereby improving the coupling between the external charger 200 and the microstimulator without the need for the user to move the position of the external charger housing 273. Such improved coupling will allow the single microstimulator to be charged faster.

Figure 6A:
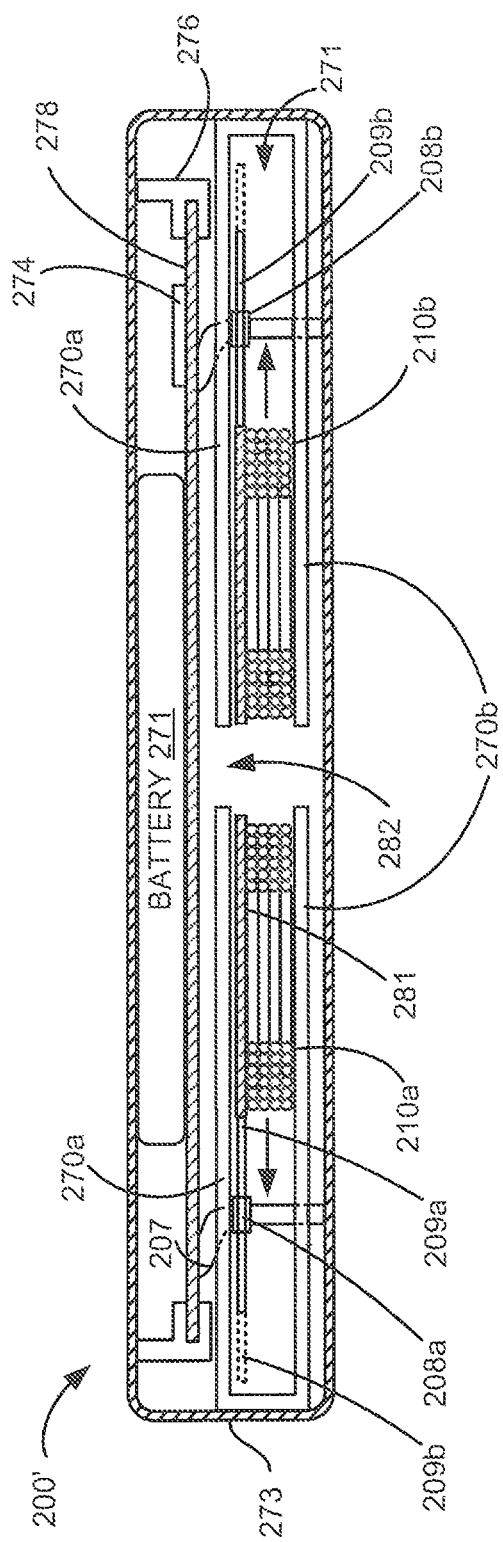
FIGS. 6A-6D illustrate the structure and operation of a second embodiment of an improved external charger comprising a plurality of charging coils mechanically positionable in unison.
Figure 6B:
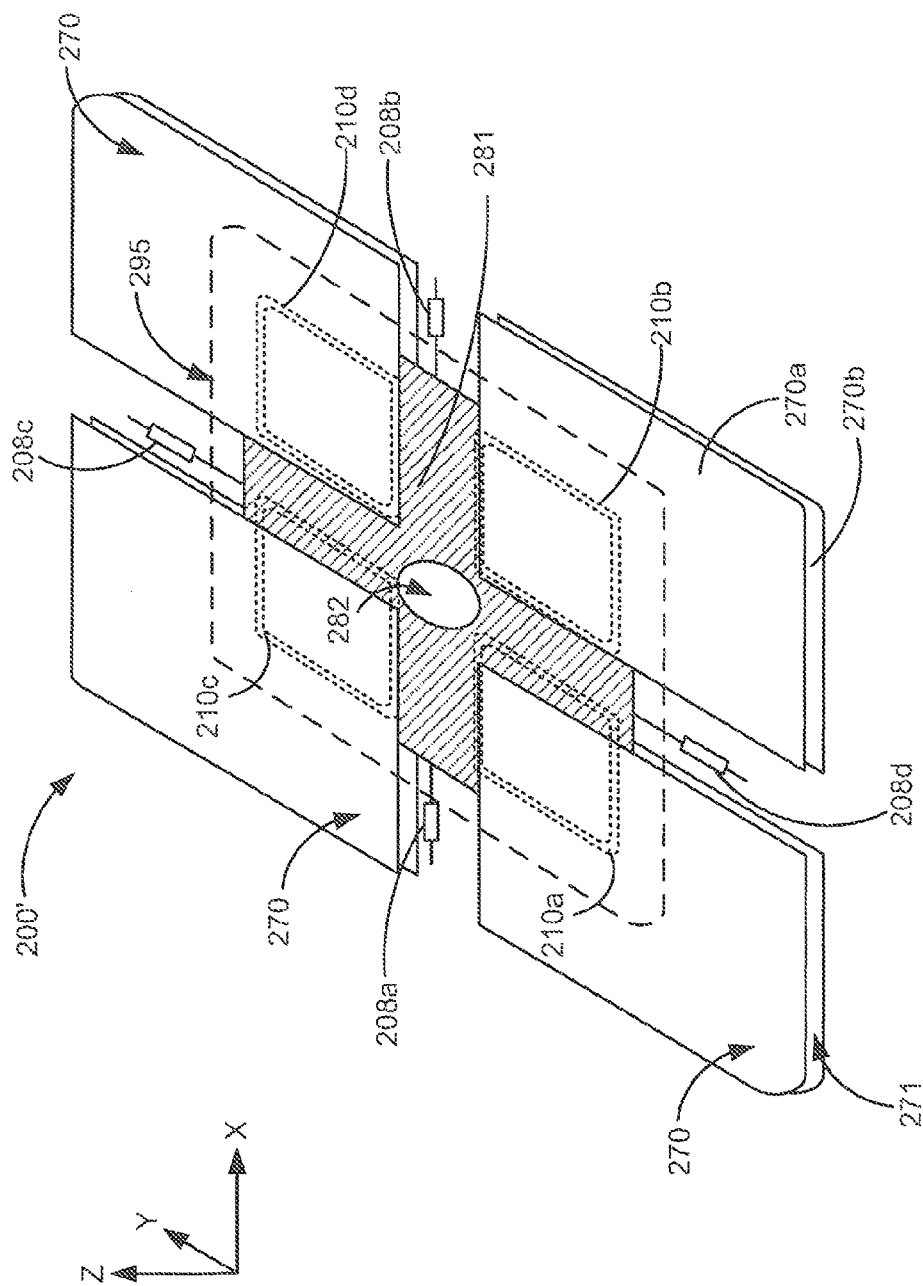
Figure 6C:
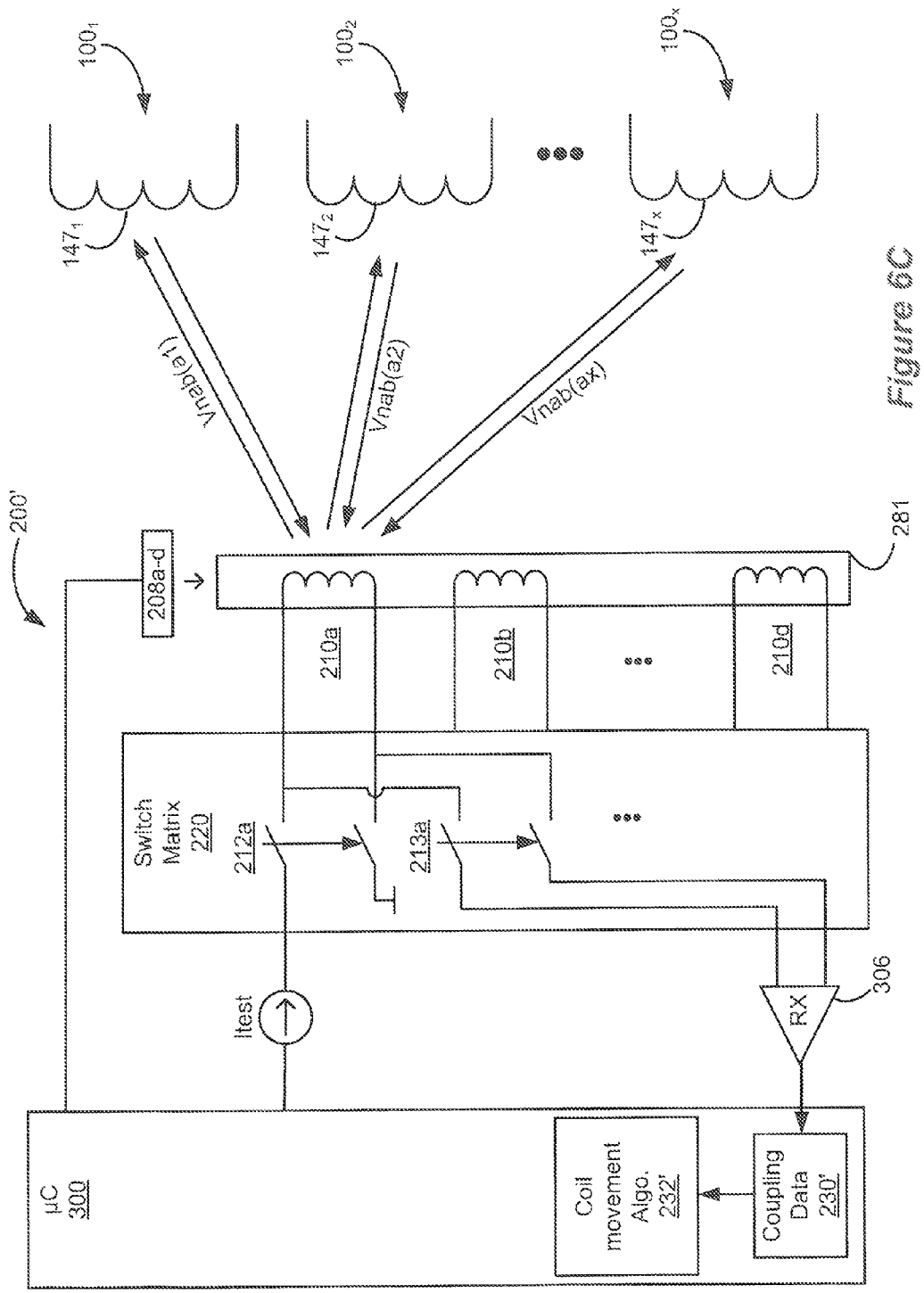

FIGS. 6A-6D illustrate another external charger 200' having a plurality of charging coils 210a-210d affixed to the coil PCB 281. The plurality of charging coils 210a-d can operate together to create a magnetic charging field for the microstimulator(s) 100. Additionally, they can be used to provide a more informed input to the coil movement algorithm 232' (FIG. 6C).

FIG. 6C illustrates circuitry involved in a testing phase in which the various coupling parameters (Vnab) between the microstimulators $100_1$ and $100_2$ and the charging coils 210a-d are deduced. A switch matrix 220 controls access to the various coils 210a-d, and each coil is associated with two groups of switches 212 and 213. Switches 212 couple their associated coil to a test current Itest, while switches 213 simultaneously couple that coil to the receiver 306. This allows each coil 210, in succession, to send a test magnetic field to each of the microstimulators 100. Each of the microstimulators 100 will send a coupling parameter (e.g., Vnab) back to the transmitting coil 210, which coil is then coupled to receiver 306 via switches 213.

As before, the reported Vnab coupling data 230' will be stored and processed by the coil movement algorithm 232'. However, and different from the Vnab values reported for the external charger 200 of FIGS. 5A-5E, the Vnab values in this instance are indexed to a particular one of the coils, as well as the implant that transmitted it. For example, Vnab(a2) represents the coupling between coil 210a and the second microstimulator $100_2$.

Figure 6D:
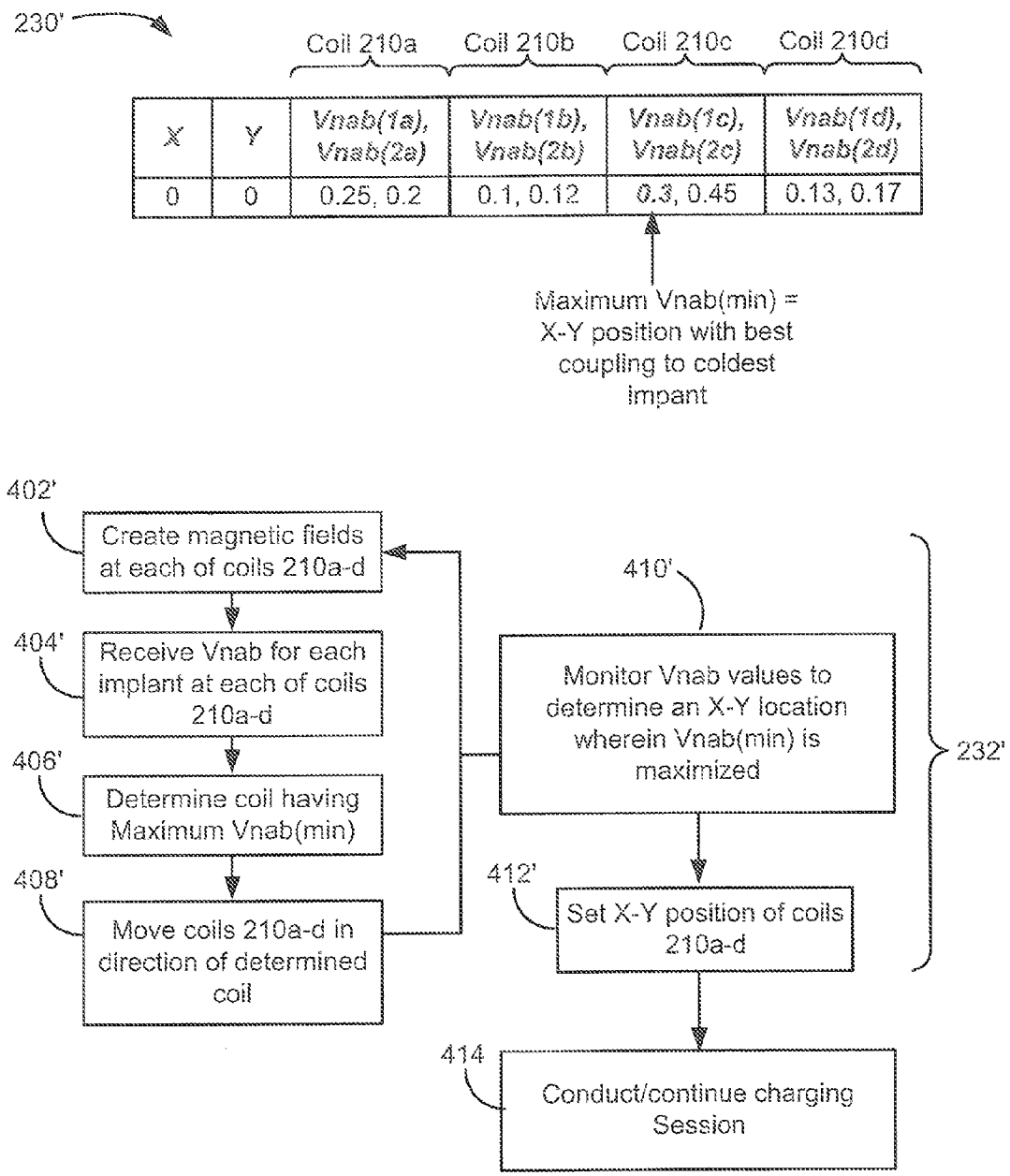

Having the Vnab values indexed in this manner allows the coil movement algorithm 232' to be modified, as shown in FIG. 6D. In step 402', a test magnetic field is created at each of the charging coils 210a-d, and the Vnab parameters for each of the implants is received as coupling data 230' in step 404'. At step 406', the algorithm 232' determines which coil has the best coupling to the weakest-coupled microstimulator, i.e., which coil has the highest value for Vnab(min). From coupling data 230', it can be seen that this comprises coil 210(c). From this, it can be inferred that the coldest implant is closest to coil 210(c), and therefore, in step 408', the coil PCB 281/coils 210a-d are moved in the direction of that coil, i.e., the coil PCB 281 with coils 210a-d is re-centered around the previous position of that coil 210(c). The process can then be repeated to fine tune the position of the coil PCB 281/coils 210a-d until in step 410' it is determined that coupling cannot be further improved, i.e., Vnab(min) is no longer increasing. This then sets the position of the coils 210a-d in step 412', and charging can commence or continue in step 414.

Although not shown in the examples to this point, an external charger 200 or 200' could additionally contain fixed coil(s) on the main PCB 278 (FIG. 5A) in addition to the coil(s) on the moveable coil PCB 281.

Figure 7B:
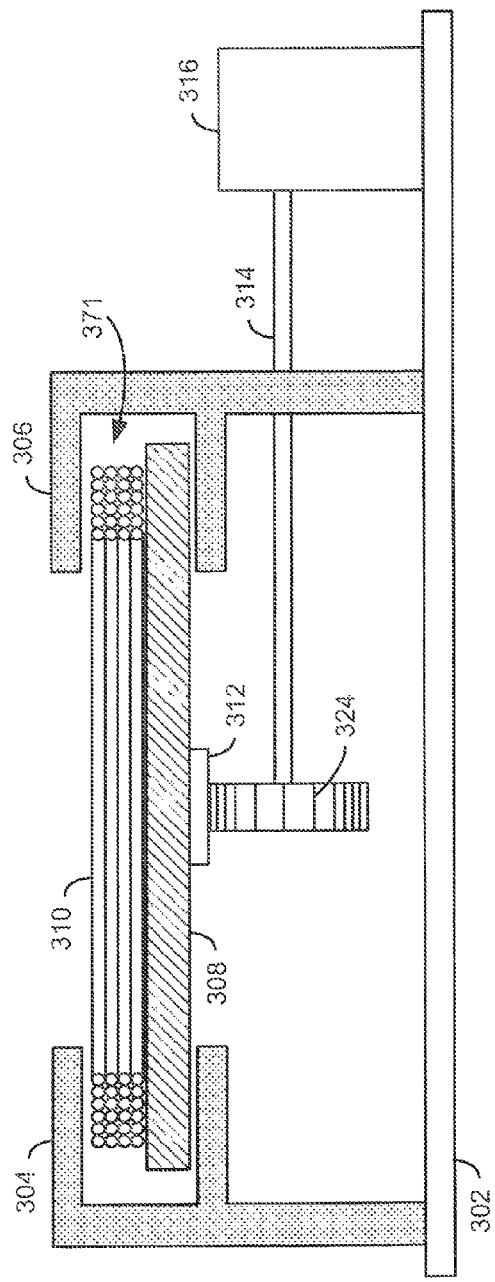

FIGS. 7A to 7G illustrate another embodiment of an improved external charger 200" that includes a plurality of charging coils 310a-c that are each independently mechanically positionable inside the housing 273 of the external charger. As shown in FIG. 7A, each of the coils 310a-c is affixed to a coil plate 308 (again referred to as a coil PCB 308 in recognition of the convenience of using this material), and each coil PCB 308/coil 310 unit rides linearly along one side of a triangular track. The triangular track is formed of an outer piece 304 and inner piece 306, which together form a coil chassis, and which may be formed of plastic and affixed within the external charger housing 273 in any number of ways. Charger 200" also contains a main PCB 302, and a plurality of mechanical actuators 316 for controlling the movement of coil PCBs 308/coils 310. A hole 320 in the main PCB 302 receives the leads from the mechanical actuators 316 and the ends of the coils 310a-c (not shown), which coil ends again should contain sufficient slack to accommodate movement of each coil 310a-c within the housing 273. Other components of the external charger 200" (e.g., the battery) are not shown for convenience.

Figure 7C:
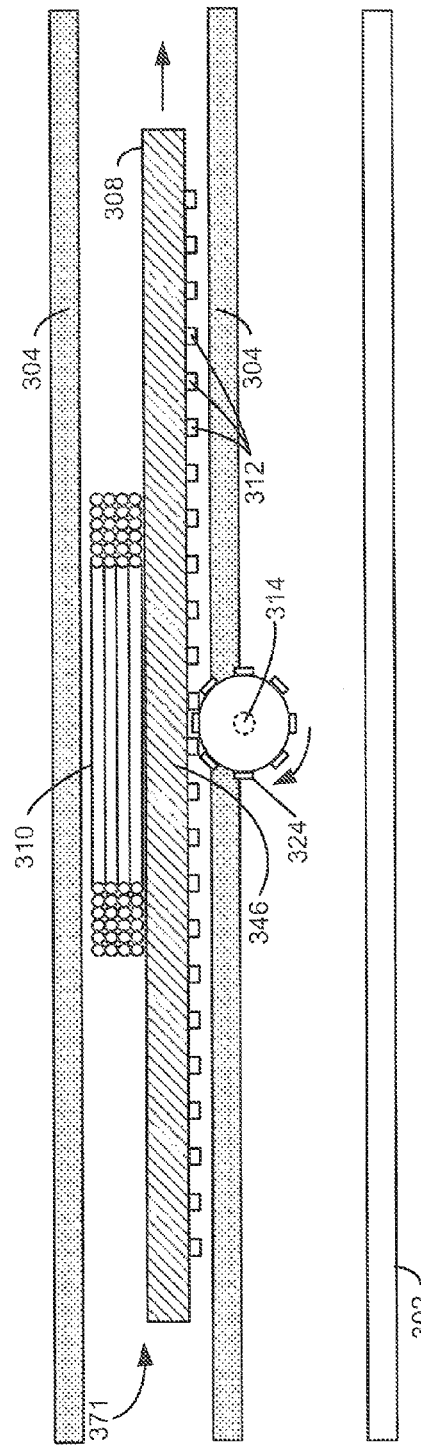

As best shown in the cross-sectional views of FIGS. 7B and 7C, the inner and outer pieces 306 have upper and lower portions to form the tracks 371 through which each coil PCB 308/coil 310 pair can move. Each coil PCB 308 may be moved by a mechanical actuator 316, such as a stepper motor that turns a crankshaft 314 having a gear 324 interfacing with teeth 312 located on the underside of the coil PCB 308. Turning the gear 324 translates into linear motion of the coil PCB 308/coil 310. Referring again to FIG. 7A, the coil PCBs 308 are generally trapezoidal in this example which allows them to move fully to one of the corners of the triangular track without interfering with movement of the other coil PCB 308 proximate to that corner. Arrow 342 shows the movement of one coil 310c all the way to the right in its track. The teeth 312 on the underside of each coil PCB 308 should be long enough to accommodate a full range of movement while at the same time limiting potential collisions between the plates.

Modifications to the design of external charger 200" are possible while still providing individual control for the mechanical positioning of each of the charging coils 310. For example, a different number of coils and tracks other than three could be provided; coils 310 could be made to move without tracks; and teeth 312 on the bottom of coil PCB 308 could be replaced or dispensed with, particularly if gear 324 is replaced by a rubber wheel, etc.

Figure 7E:
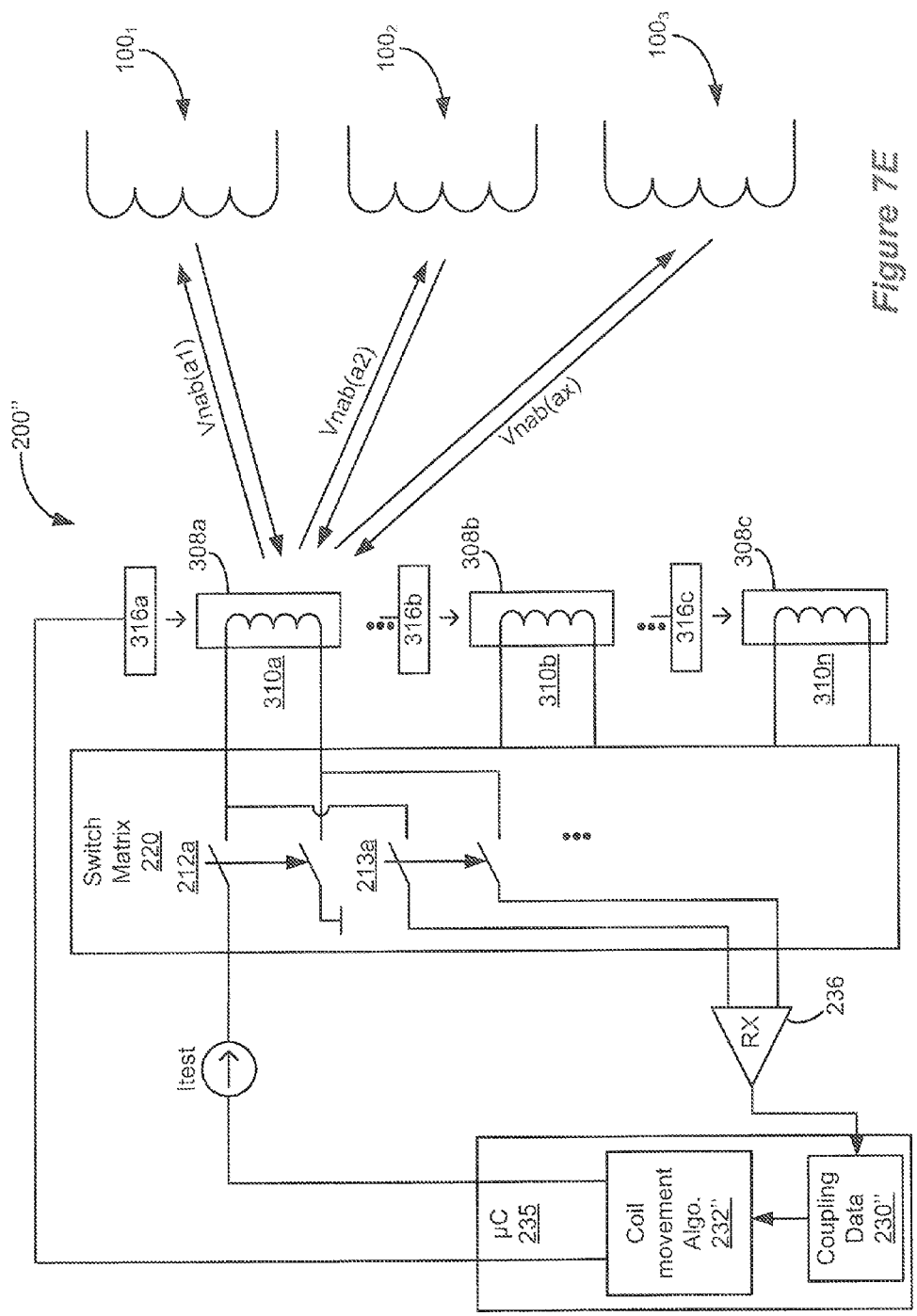

FIG. 7D shows the external charger 200" in proximity to three implanted microstimulators $100_1$, $100_2$, and $100_3$ in a top-down view, and FIG. 7E shows circuitry for positioning the coils 310a-c in an optimal position within the external charger housing 273 to charge those microstimulators. Also shown in FIG. 7D is coupling data 230" comprising the various Vnab coupling parameters between each coil 310a-c and each of the microstimulators $100_1$-$100_3$, which values were determined during a testing phase as previously described. Additionally, shown as part of the coupling data 230" are the Vnab values reported from the various microstimulators when all of the charging coils 310a-c are energized simultaneously (column 337). Unlike the remainder of coupling data 230" which is indexed to both a coil and a particular microstimulator, the column 337 data is only indexed to a particular microstimulator. The column 337 data is useful in determining an overall "coldest" implant whose coupling is in the most urgent need of improvement by mechanical manipulation of the coils 310a-c. As shown in FIG. 7D, microstimulator $100_1$ has the lowest Vnab value per column 337, and thus improvement of the coupling to that implant can be made a priority during application of the coil movement algorithm 232". This is logical, because during an actual charging session all of coils 310a-c are likely to be active, and therefore the overall coupling of the coils 310a-c to each of the microstimulators 100 is most significant. The circuitry for determining the Vnab coupling data 230" and for moving the coils 310 is shown in FIG. 7E, and is essentially the same as that shown in FIG. 6C expect for the independent mechanical control of the three PCB 308/coils 310 units by the three actuators 316a-c.

Figure 7F:
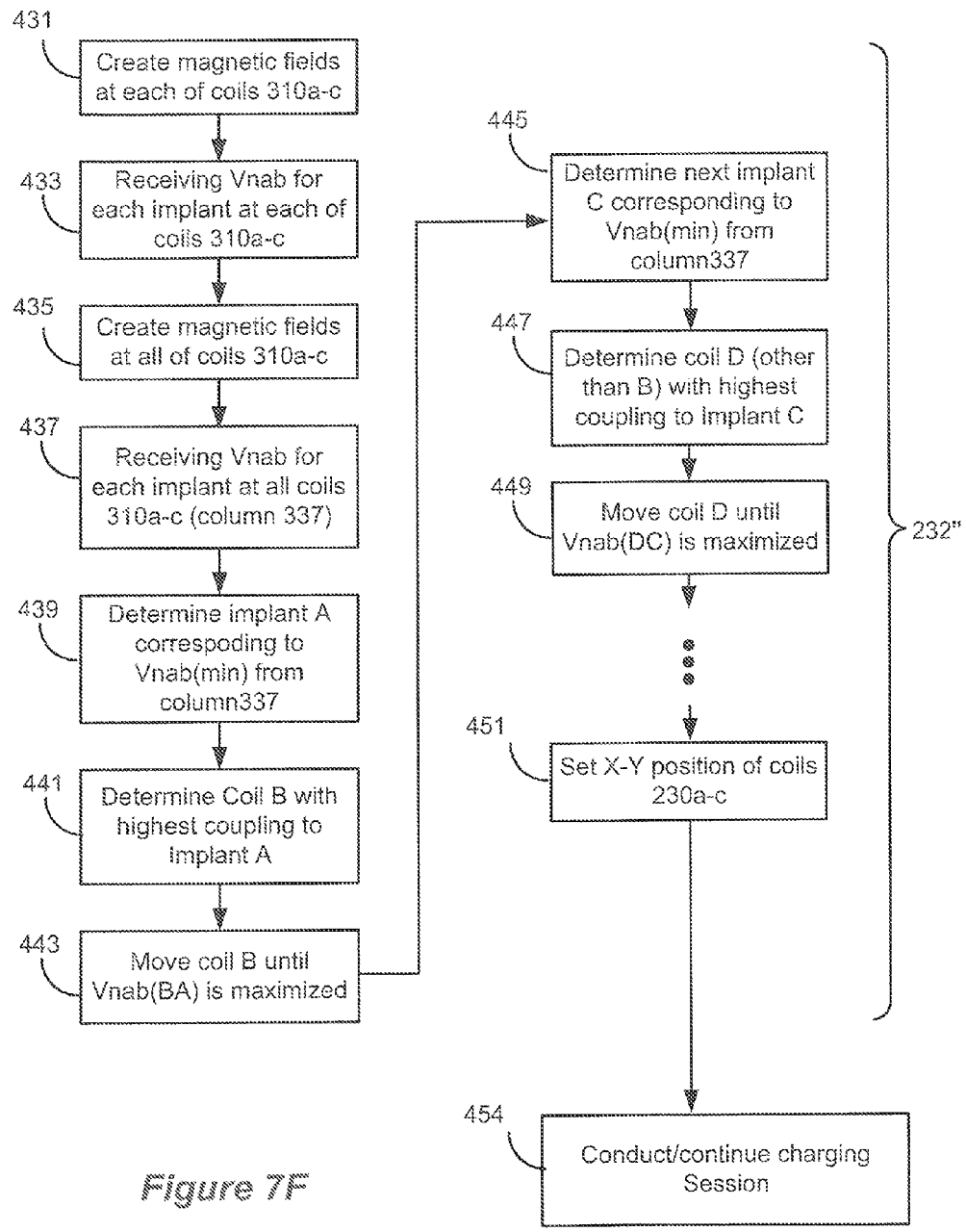

The manner in which field customization algorithm 232" can work are varied and subject to designer preferences, but one example is shown in FIG. 7F. The process begins by creating magnetic fields individually at each of the coils 310a-c (step 431), and receiving as coupling data 230" the Vnab coupling parameters between each of the coils and each of the implants 100 (step 433). Then, a magnetic field is created at all of the coils 310a-c acting together (step 435), and the Vnab parameters for each of the coils is received (step 437), which comprises column 337 in coupling data 230". From the data in column 337, an implant A is determined which generally has the lowest coupling (Vnab(min)) to the external charger 200" (step 439). In the example coupling data 232" shown in FIG. 7D, this implant A comprises microstimulator $100_1$.

Because microstimulator $100_1$ is generally the worst-coupled implant to the external charger, priority is given to improving the coupling to that microstimulator. To do so, in the next step 441, a coil B with the best coupling to implant A ($100_1$) is determined, In the example coupling data 232" shown in FIG. 7D, this coil B comprises coil 310c, because this coil has the largest Vnab value (0.20) with respect to microstimulator $100_1$. This larger coupling value suggests that coil 310c is in the best position to improve coupling to microstimulator $100_1$, and so in the next step (443) that coil 310c is moved to try and increase coupling, i.e., to maximize the Vnab value between coil 310c and microstimulator $100_1$ (Vnab(c1)). Such movement of coil 310c can occur in different manners, but generally will involve intelligently and iteratively moving coil 310c, creating a field from coil 310c, receiving Vnab from $100_1$, to eventually determine a location for coil 310c than is optimal with respect to $100_1$, i.e., where Vnab(c1) is maximized.

After Vnab(c1) is maximized, algorithm 232" turns its attention to the next-to-worst coupled implant (implant C) to the external charger 200 from again consulting column 337 of the coupling data 230" (step 445). In the example coupling data 232" shown in FIG. 7D, this implant C comprises microstimulator $100_2$, and priority is next given to optimizing that implant. To do so, in the next step 447, a coil D with the best coupling to implant C ($100_1$) is determined. However, coil B (coil 310c) is ignored at this step, because the positioning of that coil 310c was already addressed to optimize coupling to the worst coupled implant $100_1$, and it is not desired to potentially worsen coupling to $100_1$ for the benefit of improving coupling to the next-worst-coupled implant $100_2$ by once again moving coil 310c. In the example coupling data 232" shown in FIG. 7D, this coil D comprises coil 310b, because this coil has the largest Vnab value (0.22) with respect to microstimulator $100_2$. That coil 310b is then moved to try and improve coupling with respect to microstimulator $100_2$ (step 449), and the process can then continue as desired, for example, by potentially maximizing the coupling to remaining microstimulator $100_3$ if possible. Ultimately, optimal positions are set for each of the coils 310a-c (step 451), and charging can commence or continue.

Figure 7G:
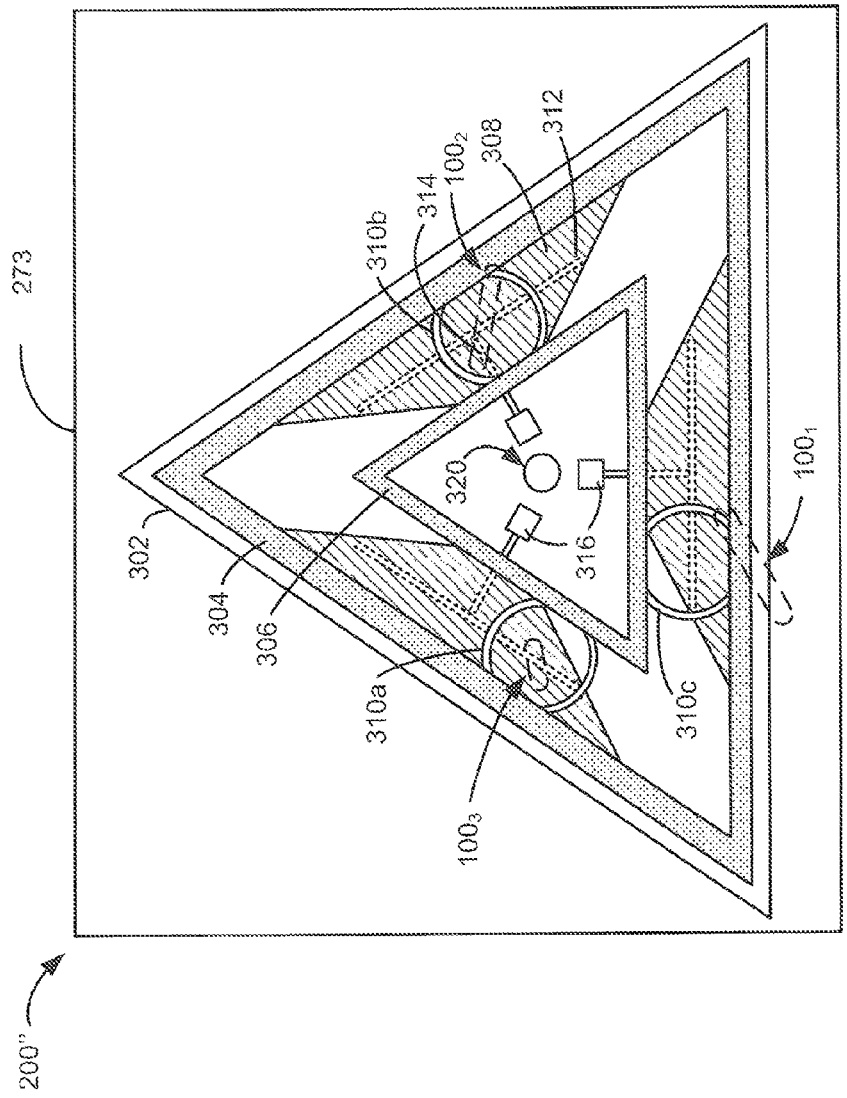

FIG. 7G shows example resulting positions for the coils 310a-c upon the application of coil movement algorithm 232", and it can be noticed that each of the coils 310 has generally been moved to be better positioned over respective ones of the microstimulators 100, which will improve coupling once coils 310a-c are used to create a magnetic charging field.

Other types of actuators can be used to move the coil(s) in X-Y directions within the external charger housing 273. For example, size-adjustable bladders or magnets could be used.

FIGS. 8A-8D illustrate an embodiment of an external charger 400 in which one or more coils are moved inside the external charger housing 273 by hand. This external charger 400 is structurally similar to the external charger 200' of FIGS. 6A-6D, in that it has a coil PCB 281 with a plurality of charging coils 210a-d. However, new to this embodiment, the external charger 400 contains handles 410a-d which extend from the sides of the housing 273 through openings 420a-d. The handles 410a-d rigidly affix to the coil PCB 281 so that it may be moved in X-Y directions in a positioning area 295 within the coil chassis 270 by a user manipulating the handles 410a-d. Although the handles 410a-d are shown as simple rods in the Figures, it should be understood that they can take on other shapes as might be easily for a user to manipulate. For example, the handles can contain grips or tabs.

External charger 400 may be used in different modes, and can take on other forms. For example, the external charger 400 may contain only one moveable charging coil 210, similar to the embodiment of FIGS. 5A-5E. In one mode, the coils 210a-d (or coil 210) can be moved within the housing 273 by the patient until an alignment indicator issues indicating good alignment (i.e., coupling) to at least one implant 100. An alignment indicator can comprise an audible sound (e.g., a beep), or the display of a light to the user, as is well known. It can also comprise the extinguishing of such indications, such that noise or lights are turned off when a suitable alignment is achieved.

Alternatively, the external charger 400 can comprise directional indicators 610 indicating in which direction the user needs to move the coil PCB 281/coils 210a-d to improve coupling to one or more implants 100. As best seen in FIG. 8C, the directional indicators 610 comprise four arrow-shaped LED lights on the housing 273, with one arrow-shaped LED light pointing towards each edge of external charger 400. When the LEDs are lit, the user is then informed as to which X-Y direction to move the handles 410a-d for improved coupling to the implant(s) 100. Circuitry and methods for determining the proper direction to move the coils 210a-d for improved coupling with the implant(s) 100 can be found in U.S. Patent Application Publication 2011/0004278 ("the '278 Publication"); and U.S. Patent Application Publication 2011/0093048 ("the '048 Publication"), each of which are incorporated herein by reference in its entirety. The '278 and '048 Publications explain how directional indicators 610 can be used to tell the user how to move the external charger housing 273 to improve coupling with the implant(s). This principle is employed in external charger 400 not to indicate how to move the external charger housing 273, but instead to indicate how to move the charging coil(s) inside of the housing 273 to improve coupling with the implant(s).

Figure 8A:
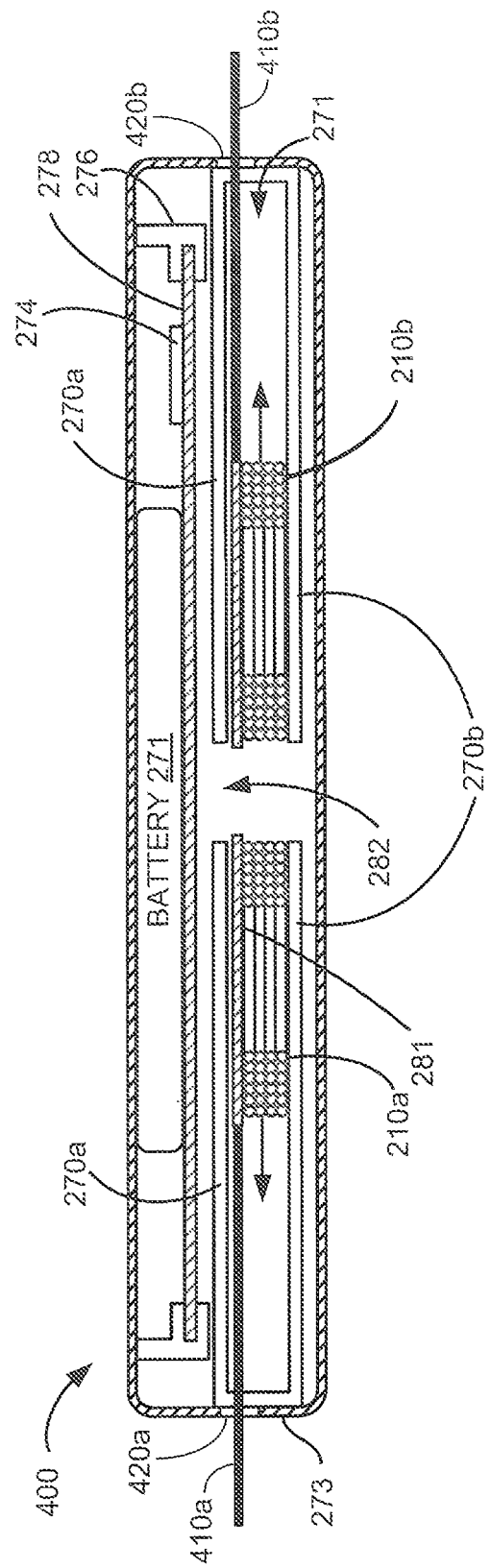
Figure 8D:
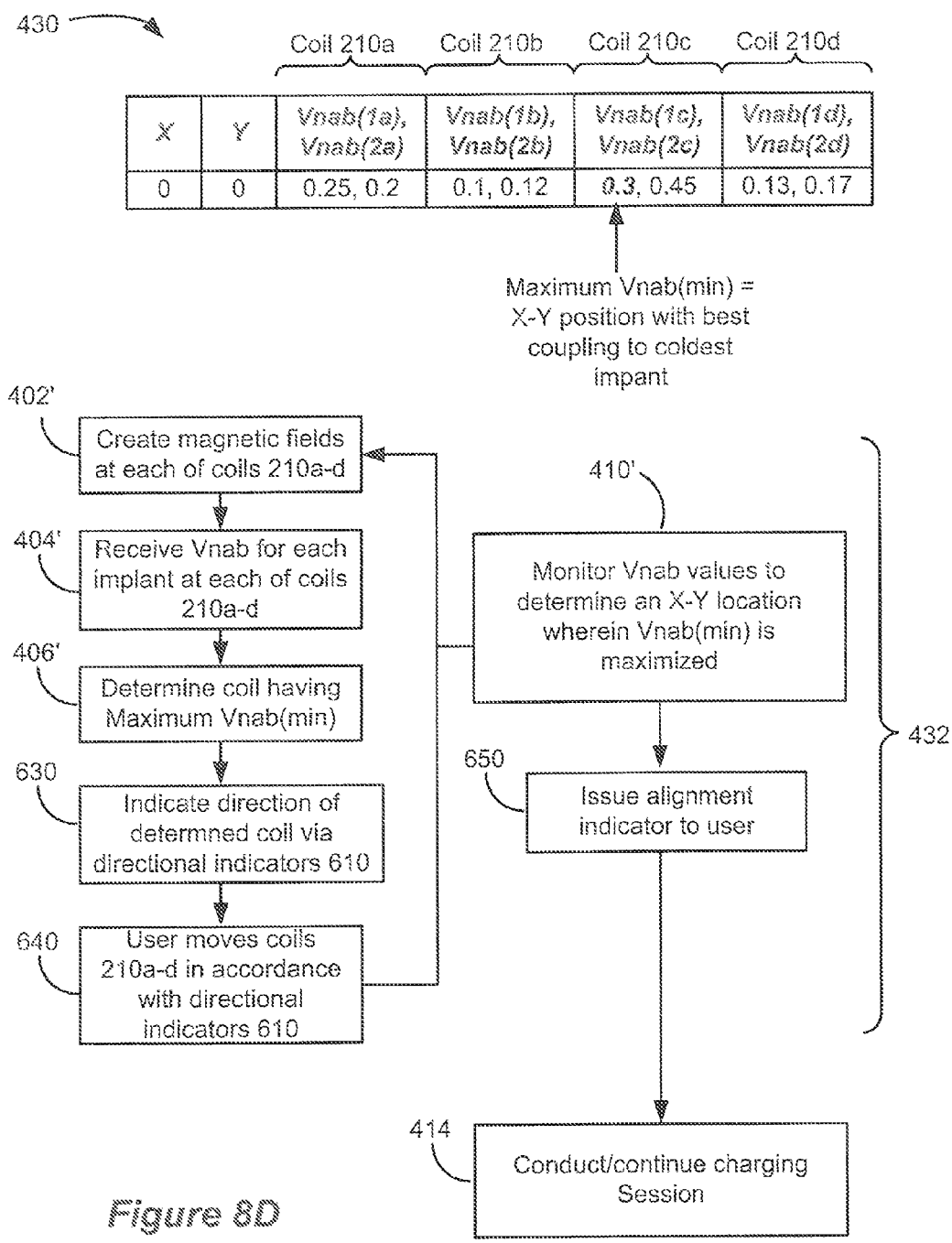

The techniques of the '278 and '048 Publications however do not provide the external charger 400 with any particular information about the implant environment—e.g., how many implants 100 are present, or the relative coupling between the external charger and those implants. FIG. 8D provides a coil movement algorithm 432 which provides such information, and which is particularly useful in charging a plurality of implants. As in prior examples of the coil movement algorithm, algorithm 432 uses the Vnab coupling data 430 as reported from each of the microstimulators 100. The algorithm 432 is similar to algorithm 232' of external charger 200' (FIGS. 6A-6D), in that it seeks to determine a coil corresponding to a maximum Vnab(min), and to move the coils 210a-d in that direction. However, instead of automatically moving the coils 210a-d in that direction, relevant directional indicators 610 are issued (or lit) (step 630), and the user then manually moves the coils 210a-d in the direction indicated (step 640). The algorithm continues to monitor this progress until Vnab(min) is not getting significantly larger (step 410'), at which point the algorithm 432 concludes that the positioning of the coils 210a-d is optimal. At this point, the external charger 400 can issue an alignment indicator (step 650), such as by extinguishing all of the directional indicators 610, to inform the user that the coupling is sufficient and that the coils do not need to be moved further. Charging can then commence or continue as in other embodiments (step 414).

Figure 9A:
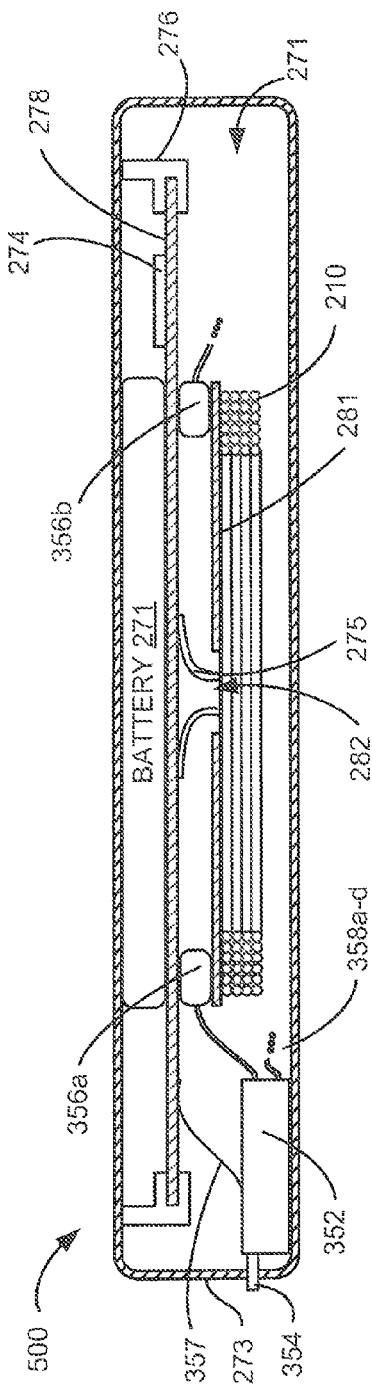
FIGS. 9A-9F illustrate the structure and operation of a fifth embodiment of an improved external charger comprising a charging coil mechanically positionable by an angular or Z-direction adjustment.
Figure 9B:
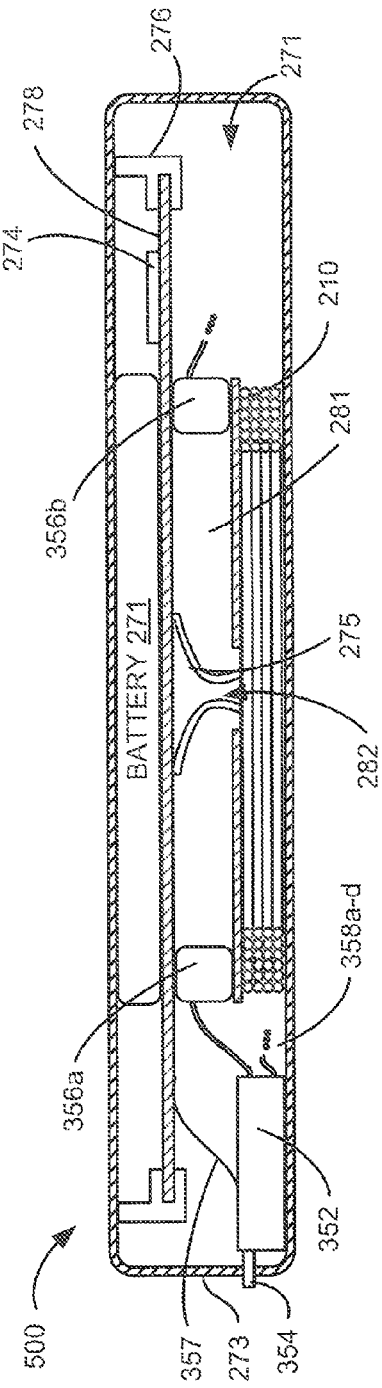
Figure 9C:
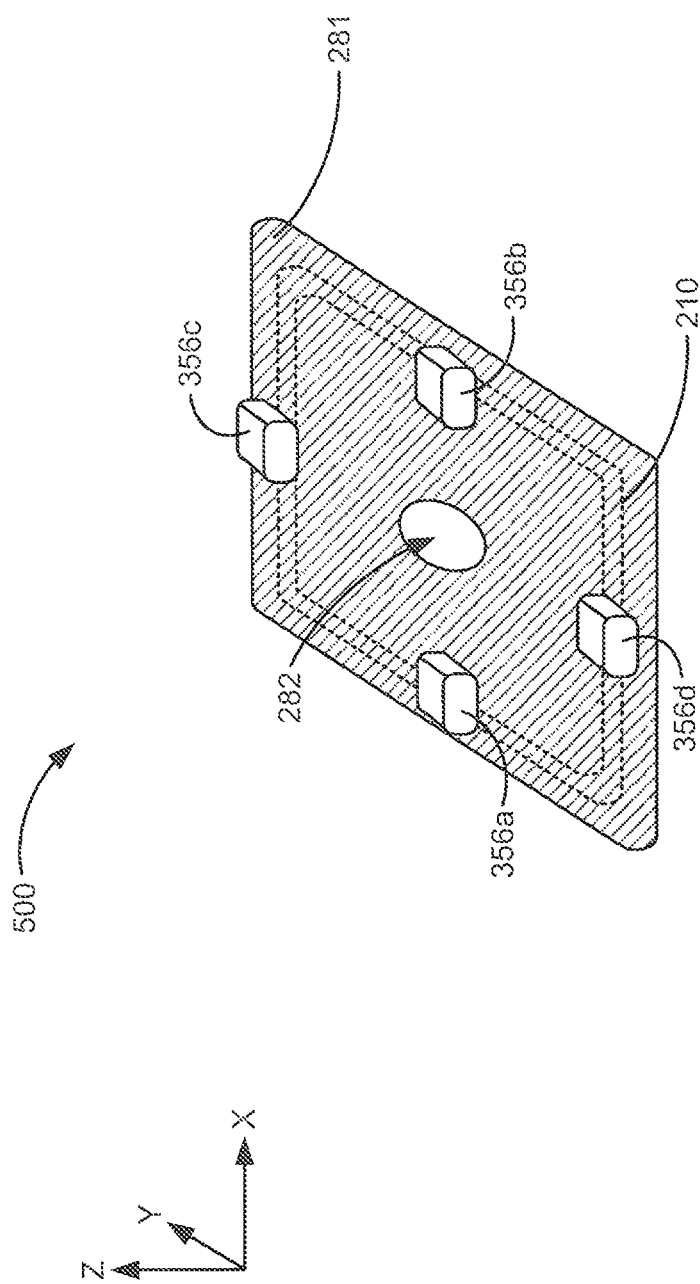

To this point in the disclosure, embodiments of improved external chargers have been illustrated in which a charging coil or coils have been moved within an external charger housing 273 in X-Y directions to improve coupling with implant(s). However, the coil(s) can be moved within the housing 273 to improve coupling in other ways, including in the Z direction, and by altering the angle of the charging coil(s). FIGS. 9A-9F illustrate such as embodiment of external charger 500. External charger 500 is generally similar in construction to the external charger 200 of FIGS. 5A-5E in that it has a coil PCB 281 with a single charging coil 210. However, and new to external charger 500, size-adjustable bladders 356a-d are included to move the coil PCB 281/coil 210 in the Z direction and to alter the angle θ of the coil within the housing 273. As shown in FIGS. 9A and 9B, the bladders 356 intervene between the main PCB 278 and the coil PCB 281, and can be inflated or deflated to move the coil PCB 281/Coil 210 in Z and angular directions. As shown in FIG. 9C, the four bladders 356 a-d are provided roughly at the edges of the coil PCB 281 to provide the desired movement. The bladders are preferably made of an elastic material, such as rubber, which will allow them to be expanded and deflated as necessary.

As seen in FIGS. 9A and 9B the bladders 365a-d are coupled to a fluid compressor 352 by tubes 358a-d respectively. The fluid compressor 352 is shown as affixed to the external charger housing 273, but may also be coupled to the main PCB 281 or elsewhere. Leads 357 to the main PCB 278 provide electrical control to the fluid compressor 352, allowing the microcontroller 300 (FIG. 9E) to selectively open and close valves (not shown) on the compressor 352 to allow it to inflate or deflect the various bladders 365a-d. The fluid compressor 352 may work with a gas or a liquid, and can be filled via port 354 extending through the side of the external charger housing 273 (FIGS. 9A and 9B).

Figure 9D:
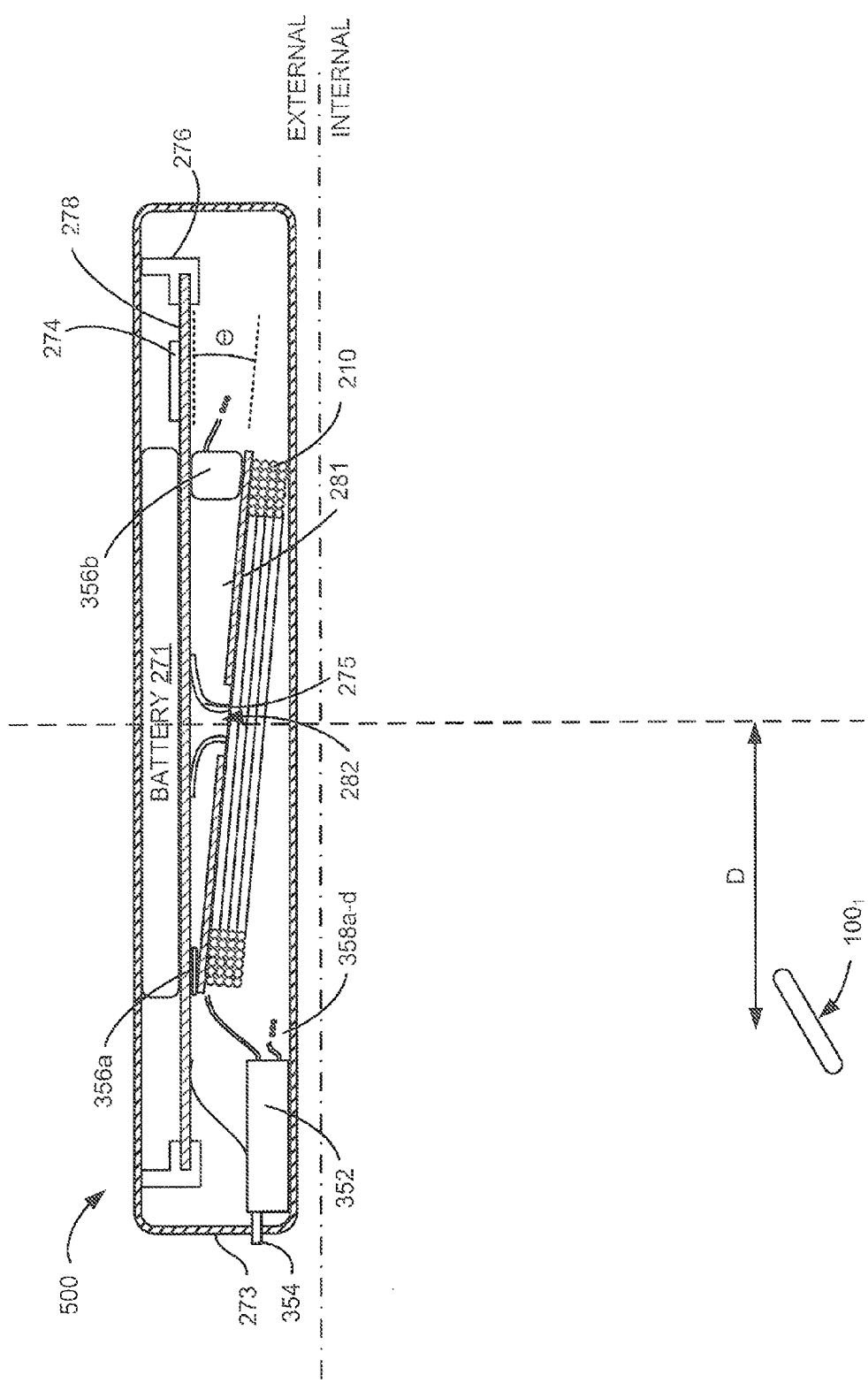
Figure 9E:
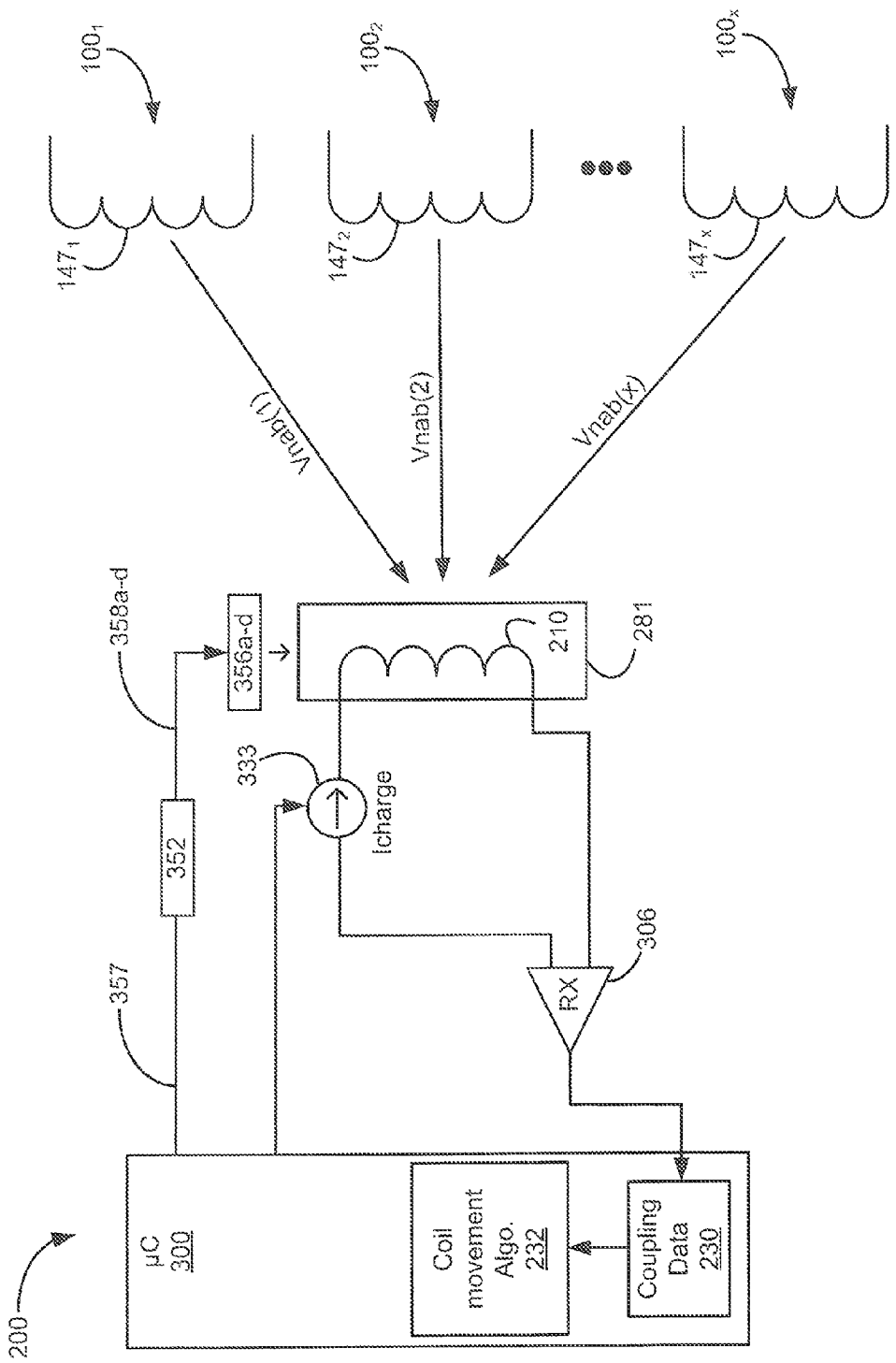

FIG. 9B shows the external charger 500 with all of the bladders 356a-d fully inflated, thus moving the coil PCB 281/coil 210 in the Z direction. FIG. 9D shows the external charger 500 with bladder 356b inflated and bladder 365a deflated, thus imparting an angle θ to the coil 210. (Bladders 356c and d (FIG. 9C) may be partially inflated). Also shown in FIG. 9D is a microstimulator 100 which is offset by a distance D from a centerline of the housing 273 of the external charger 500. In this situation, notice that the angle θ generally points the coil 210 towards the offset microstimulator 100, thus improving the coupling to it without the need to otherwise move the eternal charger 500.

Figure 9F:
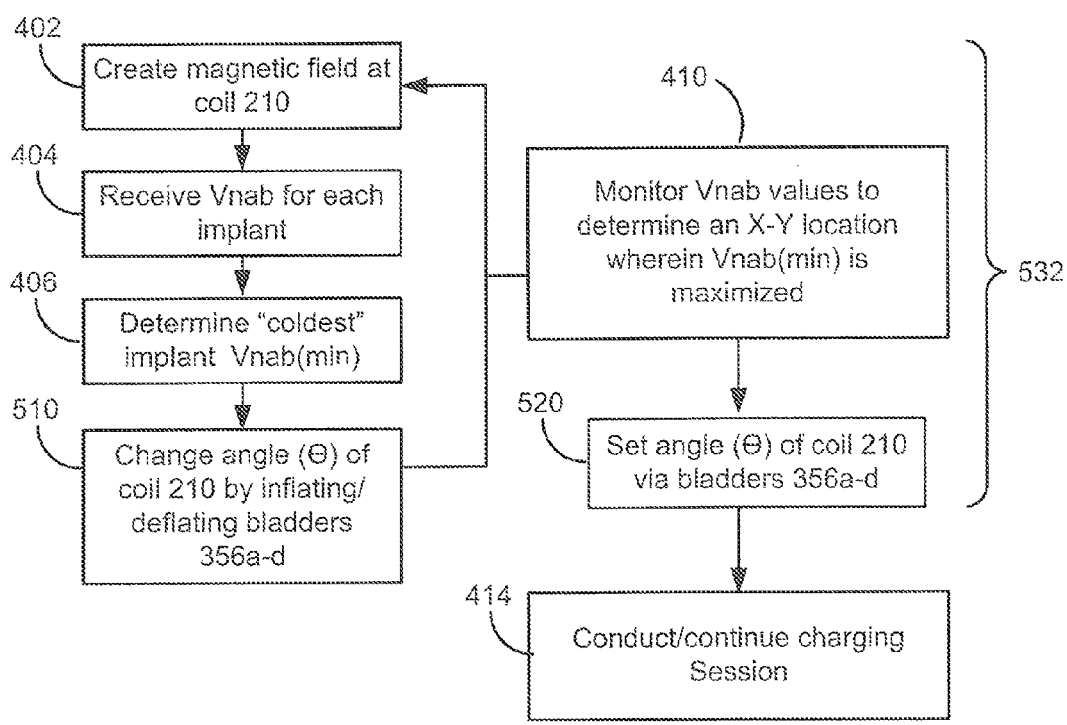

FIG. 9F illustrates one example of a coil movement algorithm 532 employed in external charger 500. The algorithm 532 is similar to the coil movement algorithm 232 of the external charger 200 (FIG. 5D), but varies in steps 510 and 520 as to how the coil 210 is angularly moved and set within the housing 273. Note that external chargers 200' (FIG. 6A-6D), 200" (FIG. 7A-FIG. 7G), and 400 (FIG. 8A-8D)

could also be modified to include angular coil movement(s), or these chargers could combine both X-Y and angular manipulation of the coil(s).

Angular movement of the coil(s) within the external charger housing 273 could be accomplished in other ways. For example, Z-motion actuators similar to the X-Y actuators 208*a-d* discussed earlier, or magnets, could be used.

Embodiments of the improved external charger to this point have highlighted the utility of simultaneously charging a plurality of microstimulators. However, it should be noted that the improved external chargers described herein can also be of benefit to charging a single microstimulator 100. The improved external charger embodiments disclosed herein benefit the charging of a single microstimulator by concentrating the magnetic charging field in locations more proximate to the vicinity of the microstimulator 100. This can result, for example, in energy savings in the production of the magnetic charging field because energy may not be spent generating significant fields at locations distant from the microstimulator.

Note that the improved external chargers disclosed herein can be used to charge implantable medical devices even if such devices do not have rechargeable batteries. For example, the external chargers can be used to provide continuous wireless power to implantable medical devices, which devices may directly rectify and use such power without storage, or using only minimal storage means such as capacitors.

While the examples provided herein have focused on moving at least one charging coil to improve coupling to at least one implantable medical device, for example, a coldest or singular implantable medical device, this is not strictly required. In other examples, at least one charging coil can be moved to decrease coupling to at least one implantable medical device, for example a hottest implantable medical devices. Adjusting the disclosed coil movement algorithms to so affect such movement is an easy modification to one skilled in the art.

The foregoing description relates to use of an improved external charger for charging neurostimulators, and in particular microstimulators. However, it is to be understood that the invention is not so limited. Rather, the invention may be used with any type of implantable medical device system that could benefit from improved charging techniques. For example, the present invention may be used as part of a system employing one or more of an implantable sensor, an implantable pump, a pacemaker, a defibrillator, a cochlear stimulator, a retinal stimulator, a spinal cord stimulator, a stimulator configured to produce coordinated limb movement, a cortical and deep brain stimulator, or with any other neural stimulator configured to treat any of a variety of conditions.

While the inventions disclosed have been described by means of specific embodiments and applications thereof, numerous modifications and variations could be made thereto by those skilled in the art without departing from the literal and equivalent scope of the claims set forth herein.

What is claimed is:

1. An external charger for charging at least one implantable medical device using a magnetic charging field, comprising:
   a housing; and
   at least one charging coil within the housing, and control circuitry configured to move the at least one charging coil,
   wherein the control circuitry is configured to move the at least one charging coil to a position within the housing in accordance with at least one measured parameter, wherein each measured parameter is indicative of the coupling between the external charger and one of the one or more implantable medical devices.

2. The external charger of claim 1, wherein the housing is sized to be hand holdable.

3. The external charger of claim 1, wherein the housing comprises a planar surface.

4. The external charger of claim 3, wherein the at least one coil is moveable in a plane parallel to the planar surface.

5. The external charger of claim 3, wherein the at least one coil is moveable in a direction perpendicular to the planar surface.

6. The external charger of claim 3, wherein the at least one coil is moveable at an angle with respect to the planar surface.

7. The external charger of claim 1, wherein the at least one coil is moveable using at least one motor within the housing.

8. The external charger of claim 1, wherein the at least one coil is moveable using at least one size-adjustable bladder within the housing.

9. The external charger of claim 1, wherein the at least one coil is manually moveable.

10. The external charger of claim 9, wherein the at least one coil is manually moveable using at least one handle external to the housing.

11. The external charger of claim 1, wherein the external charger comprises a plurality of charging coils.

12. The external charger of claim 11, wherein the charging coils are moveable within the housing in unison.

13. The external charger of claim 11, wherein the charging coils are each independently moveable within the housing.

14. The external charger of claim 1, further comprising a memory for storing the at least one measured parameter indicative of the coupling between the external charger and the at least one implantable medical device, and wherein the at least one charging coil is moveable within the housing in accordance with an algorithm which receives the at least one coupling measured parameter.

15. The external charger of claim 1, further comprising a microcontroller for executing an algorithm for moving the at least one charging coils.

16. The external charger of claim 1, further comprising a directional indicator on the housing to indicate in which direction a user should move the at least one charging coil within the housing.

17. A method for optimizing charging of one or more implantable medical device using an external charger, the method comprising:
   automatically measuring at least one parameter, wherein each measured parameter is indicative of the coupling between the external charger and one of the one or more implantable medical devices; and
   automatically moving at least one charging coil in the external charger to a position determined by a control circuit in accordance with the at least one measured parameter.

18. The method of claim 17, wherein moving the at least one charging coil improves coupling to at least one implantable medical device.

19. The method of claim 18, wherein the at least one charging coil is moved to improve coupling to an implantable medical device having a worst coupling to the external charger.

20. The method of claim 17, wherein moving the at least one charging coil decreases coupling to at least one implantable medical device.

21. The method of claim 17, wherein the at least one parameter is measured at the implantable medical device, and further comprising receiving the at least one parameter via telemetry from the one or more implantable medical devices.

22. The method of claim 17, wherein the at least one parameter is measured during producing a magnetic field at one or more of the charging coils.

23. The method of claim 17, wherein the external charger comprises a plurality of coils, and wherein each measured parameter is indicative of the coupling between a particular one of the charging coils and a particular one of the one or more implantable medical devices.

24. The method of claim 17, further comprising assessing the at least one measured parameter to indicate to the user in which direction to move the at least one charging coil.

25. The method of claim 17, wherein the at least one charging coil is automatically moved in accordance with an algorithm executed by a microcontroller within the external charger, wherein the algorithm receives the at least one measured parameter.

26. The method of claim 17, wherein the at least one measured parameter comprises a parameter from a power circuitry of the one or more implantable medical devices.

27. The method of claim 17, wherein the at least one measured parameter comprises a temperature of the one or more implantable medical devices.

28. The method of claim 17, wherein the method is performed during a testing phase before charging the one or more implantable medical devices during a charging session.

29. The method of claim 17, wherein the method is performed while charging the one or more implantable medical devices during a charging session.

30. The method of claim 17, wherein the at least one charging coil is located in a plane, and wherein the at least one charging coil is moveable in the plane.

31. The method of claim 17, wherein the at least one charging coil is located in a plane, wherein the at least one charging coil is moveable in a direction perpendicular to the plane.

32. The method of claim 17, wherein the at least one charging coil is located in a plane, wherein the at least one coil is moveable at an angle with respect to the plane.

33. The method of claim 17, wherein the at least one coil is moveable by hand.

34. The method of claim 17, wherein the external charger comprises a plurality of charging coils, and wherein the charging coils are moved in unison.

35. The method of claim 17, wherein the external charger comprises a plurality of charging coils, and wherein the charging coils are each independently moved.

* * * * *